US008676383B2

(12) United States Patent
Tan et al.

(10) Patent No.: US 8,676,383 B2
(45) Date of Patent: Mar. 18, 2014

(54) DEVICE FOR CARRYING OUT CHEMICAL OR BIOLOGICAL REACTIONS

(75) Inventors: Lim Hi Tan, Singapore (SG); Jew Kwee Ngui, Singapore (SG); Hon Siu Shin, Singapore (SG); Ui Leng Soh, Singapore (SG); Yang Hooi Kee, Singapore (SG); Hock Lai Khoo, Singapore (SG); Mark T. Reed, Menlo Park, CA (US); Ching Ong Lau, Singapore (SG); Wolfgang Heimberg, Ebersberg (DE)

(73) Assignee: Applied Biosystems, LLC, Carlsbad, CA (US)

( * ) Notice: Subject to any disclaimer, the term of this patent is extended or adjusted under 35 U.S.C. 154(b) by 1043 days.

(21) Appl. No.: 11/850,345

(22) Filed: Sep. 5, 2007
(Under 37 CFR 1.47)

(65) Prior Publication Data
US 2008/0274511 A1 Nov. 6, 2008

Related U.S. Application Data

(63) Continuation-in-part of application No. 11/470,463, filed on Sep. 6, 2006, and a continuation-in-part of application No. 10/089,136, filed on Dec. 23, 2002.

(60) Provisional application No. 60/680,891, filed on May 13, 2005.

(51) Int. Cl.
G05B 21/00 (2006.01)
(52) U.S. Cl.
USPC .......................... 700/266; 700/268; 435/303.1
(58) Field of Classification Search
USPC .............. 436/50, 55; 422/102, 105, 108, 109; 435/303.1
See application file for complete search history.

(56) References Cited

U.S. PATENT DOCUMENTS

| | | | |
|---|---|---|---|
| 3,036,893 A | 5/1962 | Natelson | |
| 3,128,239 A | 4/1964 | Page | |
| 3,216,804 A | 11/1965 | Natelson | |
| 3,260,413 A | 7/1966 | Natelson | |
| 3,261,668 A | 7/1966 | Natelson | |
| 3,271,112 A | 9/1966 | Williams et al. | |
| 3,331,665 A | 7/1967 | Natelson | |
| 3,368,872 A | 2/1968 | Natelson | |
| 3,556,731 A | 1/1971 | Martin | |
| 4,865,986 A | 9/1989 | Coy et al. | |
| 4,950,608 A | 8/1990 | Kishimoto | |
| 5,038,852 A | 8/1991 | Johnson et al. | |
| 5,061,630 A | 10/1991 | Knopf et al. | |
| 5,224,536 A | 7/1993 | Eigen et al. | |
| 5,333,675 A | 8/1994 | Mullis et al. | |
| 5,430,957 A | 7/1995 | Eigen et al. | |
| 5,441,576 A | 8/1995 | Bierschenk et al. | |
| 5,475,610 A * | 12/1995 | Atwood et al. ................ 700/269 |
| 5,525,300 A | 6/1996 | Danssaert et al. | |
| 5,601,141 A | 2/1997 | Gordon et al. | |
| 5,656,493 A | 8/1997 | Mullis et al. | |
| 5,716,842 A | 2/1998 | Baier et al. | |
| 5,819,842 A * | 10/1998 | Potter et al. .................... 165/206 |
| 5,871,908 A | 2/1999 | Henco et al. | |
| 6,093,370 A | 7/2000 | Yasuda et al. | |
| 6,525,550 B2 | 2/2003 | Pan | |
| 6,558,947 B1 | 5/2003 | Lund et al. | |
| 6,633,785 B1 | 10/2003 | Kasahara et al. | |
| 6,767,512 B1 | 7/2004 | Lurz et al. | |
| 6,814,934 B1 | 11/2004 | Higuchi | |
| 6,825,047 B1 | 11/2004 | Woudenberg et al. | |
| 2001/0001644 A1 | 5/2001 | Coffman et al. | |
| 2004/0241048 A1 | 12/2004 | Shin et al. | |
| 2006/0024816 A1 | 2/2006 | Fawcett et al. | |
| 2006/0228268 A1 | 10/2006 | Heimberg et al. | |

FOREIGN PATENT DOCUMENTS

| | | |
|---|---|---|
| DE | 1 900 279 | 9/1969 |
| DE | 1 964 6115 | 5/1998 |
| EP | 0 089 383 | 9/1983 |
| EP | 0 488 769 | 6/1992 |
| EP | 0 545 736 | 6/1993 |
| EP | 0 776 967 | 6/1997 |
| EP | 081 262 | 12/1997 |
| WO | WO 89/12502 | 12/1989 |
| WO | WO 90/05947 | 5/1990 |
| WO | WO 92/04979 | 4/1992 |

(Continued)

OTHER PUBLICATIONS

Translation of portions of German patent specification DE 19646115 A1.
Translation of the claims of International patent specification WO 98/20975.
German Patent Office Search Report for corresponding DE 29917313.5.
"LightCycler® 480 System *Rapid by Nature—Accurate by Design*" brochure, Roche Diagnostics, 16 pages, printed from www.roche-applied-science.com, undated.
"CoolerMaster Expand Your Imagination, Hyper 6 (KHC-V81)," printed from http://www.coolermaster.com/index.php?LT=english&Language_s=2&url_place=product&p_serial=KHC-V81&oth on May 8, 2006, pp. 1-5.
"Cooling Machine CPU Cooler, Thermaltake," printed from http://www.thermaltake.com/coolers/4in1heatpipe/cl-p0114bigtyphoon/cl-p0114.htm on May 8, 2006, pp. 1-2, Copyright 2003.

(Continued)

Primary Examiner — Natalia Levkovich

(57) ABSTRACT

The invention relates to a device for carrying out of chemical or biological reactions with a reaction vessel receiving element for receiving a microtiter plate with several reaction vessels, wherein the reaction vessel receiving element has several recesses arranged in a regular pattern to receive the respective reaction vessels, a heating device for heating the reaction vessel receiving element, and a cooling device for cooling the reaction vessel. The invention is characterized by the fact that the reaction vessel receiving element is divided into several segments. The individual segments are thermally decoupled from one another, and each segment is assigned a heating device which may be actuated independently of the others. By means of the segmentation of the reaction vessel receiving element, it is possible for zones to be set and held at different temperatures. Because the reaction vessel receiving element is suitable for receiving standard microtiter plates, the device according to the invention may be integrated in existing process sequences.

24 Claims, 20 Drawing Sheets

(56) References Cited

FOREIGN PATENT DOCUMENTS

WO    WO 95/11294    4/1995
WO    WO 98/20975    5/1998
WO    WO 01/24930    4/2001

OTHER PUBLICATIONS

Stratagene,.Quantitative PCR Systems, May 2006, pp. 1-12.
Notification of Transmittal of the International Search Report, International Searching Authority, International Application No. PCT/US07/77696, Jul. 14, 2008, 9 Pages.

* cited by examiner

DEVICE FOR CARRYING OUT CHEMICAL OR BIOLOGICAL REACTIONS

RELATED APPLICATIONS

This application is a continuation-in-part of application Ser. No. 11/470,463, filed Sep. 6, 2006, which claims the benefit of U.S. Provisional Application No. 60/680,891 filed on May 13, 2005, and is a continuation in part of application Ser. No. 10/089,136, filed Dec. 23, 2002, all of which are incorporated herein by reference in their entirety.

FIELD OF THE INVENTION

The present invention relates to a device for the carrying out of chemical or biological reactions with a reaction vessel receiving element for receiving reaction vessels, wherein the reaction vessel receiving element—has several recesses arranged in a pattern to receive reaction vessels, a heating element for heating the reaction vessel receiving element, and a cooling device for cooling the reaction vessel receiving element.

INTRODUCTION

Testing of biological or chemical samples often requires a device for repeatedly subjecting multiple samples though a series of temperature cycles. Such devices are described as thermocyclers or thermocycling devices and are used to generate specific temperature cycles, i.e. to set predetermined temperatures in the reaction vessels and to maintain predetermined intervals of time.

A conventional device of this kind is known from U.S. Pat. No. 5,525,300. The disclosed device has four reaction vessel receiving elements, each with recesses arranged in a regular pattern. The pattern of the recesses corresponds to a known pattern of reaction vessels of standard microtiter plates, so that microtiter plates with their reaction vessels may be inserted in the recesses.

The heating and cooling devices of a reaction vessel receiving element are so designed that a stepped temperature gradient extending over the reaction vessel receiving element may be generated. This means that, during a temperature cycle, different temperatures may be obtained in the individual reaction vessels. This makes it possible to carry out certain experiments at different temperatures simultaneously.

This stepped temperature gradient is used to determine the optimal denaturing temperature, the optimal annealing temperature, and the optimal elongation temperature of a PCR reaction. To achieve this, the same reaction mixture is poured into the individual reaction vessels, and the temperature cycles necessary to perform the PCR reaction are executed. Such a temperature cycle comprises the heating of the reaction mixture to the denaturing temperature, which usually lies in the range 90°-95° C., cooling to the annealing temperature, which is usually in the range 40°-60° C. and heating to the elongation temperature, which is usually in the range 70°-75° C. If desired, the time of each cycle can also be varied. A cycle of this kind is repeated several times, leading to amplification of a predetermined DNA sequence.

Since a stepped temperature gradient can be set, different but predetermined temperatures are set in the individual reaction vessels. After completion of the cycles it is possible to determine, with the aid of the reaction products, those temperatures at which the PCR reaction will give the user the optimal result. Here the result may be optimised e.g. in respect of product volume or also product quality.

The annealing temperature, at which the primer is added, has a powerful influence on the result. However the elongation temperature too can have beneficial or adverse effects on the result. At a higher elongation temperature, the addition of the bases is accelerated, with the probability of errors increasing with higher temperature. In addition, the life of the polymerase is shorter at a higher elongation temperature.

A thermocycling device, by which the stepped temperature gradient may be set, makes it much easier to determine the desired temperatures, since a reaction mixture may simultaneously undergo cycles at different temperatures in a single thermocycling device.

Another important parameter for the success of a PCR reaction is the different residence volumes spread over different reaction vessels. Problems arise with conventional devices as these parameters can not be varied in one test series for an individual reaction vessel holder. To test different residence volumes, several test series are required and are performed either consecutively in one thermocycling device or simultaneously in several thermocycling devices.

For this purpose there are so-called multiblock thermocycling devices with several reaction vessel receiving elements, each provided with separate cooling, heating and control devices (see U.S. Pat. No. 5,525,300). The reaction mixture to be tested must be distributed over several microtiter plates, for testing independently of one another.

Problems arise in determining the optimal residence times, rates of temperature change, and residence volumes using conventional thermocycling devices because it is necessary to have either several thermocycling devices or a multiblock thermocycling device, or to carry out tests in several consecutive test series. The acquisition of several thermocycling devices or of a multiblock thermocycling device is costly and the carrying-out of several consecutive test series takes too long. In addition, handling is laborious when only part of the reaction vessels of several microtiter plates is filled, with each of the latter being tested and optimised in separate test series. This is especially disadvantageous in the case of devices which operate automatically and in which the reaction mixtures are subject to further operations, since several microtiter plates must then be handled separately. It is also extremely impractical when only part of the reaction vessels of the microtiter plates is filled, since the devices for further processing, such as e.g. sample combs for transferring the reaction products to an electrophoresis apparatus, are often laid out on the grid of the microtiter plates, which means that further processing is correspondingly limited if only part of the reaction vessels of the microtiter plate is used.

U.S. Pat. No. 5,819,842 discloses a device for the individual, controlled heating of several samples. This device has several flat heating elements arranged in a grid pattern on a work surface. Formed below the heating elements is a cooling device which extends over all the heating elements. In operation a specially designed sample plate is placed on the work surface. This sample plate has a grid plate, covered on the underside by a film. The samples are poured into the recesses of the grid plate. In this device the samples lie on the individual heating elements, separated from them only by the film. By this means, direct heat transfer is obtained. Problems arise with this device because specially designed microtiter plates must be used and commonly available ones cannot be used.

Moreover, with increasing automation in biotechnology, thermocyclers are increasingly being used in automated production lines and with robots as one of several work stations. Here it is customary for the samples to be passed in microtiter plates from one work station to the next. Problems arise with the thermocycler disclosed by U.S. Pat. No. 5,819,842 as it would be necessary for the samples to be pipetted out of a microtiter plate into the specially designed sample plate before temperature adjustment, and from the sample plate into a microtiter plate after temperature adjustment. Here there is a risk of contamination of the samples. The use of this specially designed sample plate must therefore be regarded as extremely disadvantageous.

Thus, there is a need to overcome these and other problems of the prior art to provide a method and system for controlling the temperature of a sample block of a thermocycler.

SUMMARY OF THE INVENTION

According to various embodiments, the present teachings include a thermocycler for processing biological or chemical samples. The thermocycler can include a sample block configured to receive one microtiter plate and configured to define a plurality of zones and a thermoelectric cooling device (TEC) disposed in each of the plurality of zones, wherein the TEC provides course heating of the zone to near a control temperature. The thermocycler can further include a heating element disposed in each of the plurality of zones, wherein the heating element provides fine heating of the zone to about the control temperature.

According to various embodiments, the present teachings also include a system for processing biological or chemical samples. The system can include a sample block defining a plurality of zones and a detachable microtiter plate configured to detach into a plurality of segments, wherein the plurality of segments correspond to the plurality of zones. The system can further include a thermoelectric cooling device (TEC) disposed in each of the plurality of zones and a temperature sensor disposed in each of the plurality of zones. The system can also include a heating element disposed in each of the plurality of zones, wherein the TEC provides course heating of the zone and the heating element provides fine heating of the zone.

According to various embodiments, the present teachings further include a method for processing biological or chemical samples. The method can include denaturing samples in a first portion of a microtiter plate at a temperature $T_{d1}$ by heating a first zone of a sample block, wherein a first thermo electric cooling device (TEC) provides coarse heating of the first zone to a temperature near $T_{d1}$ and a first heating element provides fine heating of the first zone to about $T_{d1}$. The method can also include denaturing samples in a second portion of the microtiter plate at a temperature $T_{d2}$ by heating a second zone of the sample block, wherein a second thermo electric cooling device (TEC) provides coarse heating of the second zone to a temperature near $T_{d2}$ and a second heating element provides fine heating of the second zone to about $T_{d2}$.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
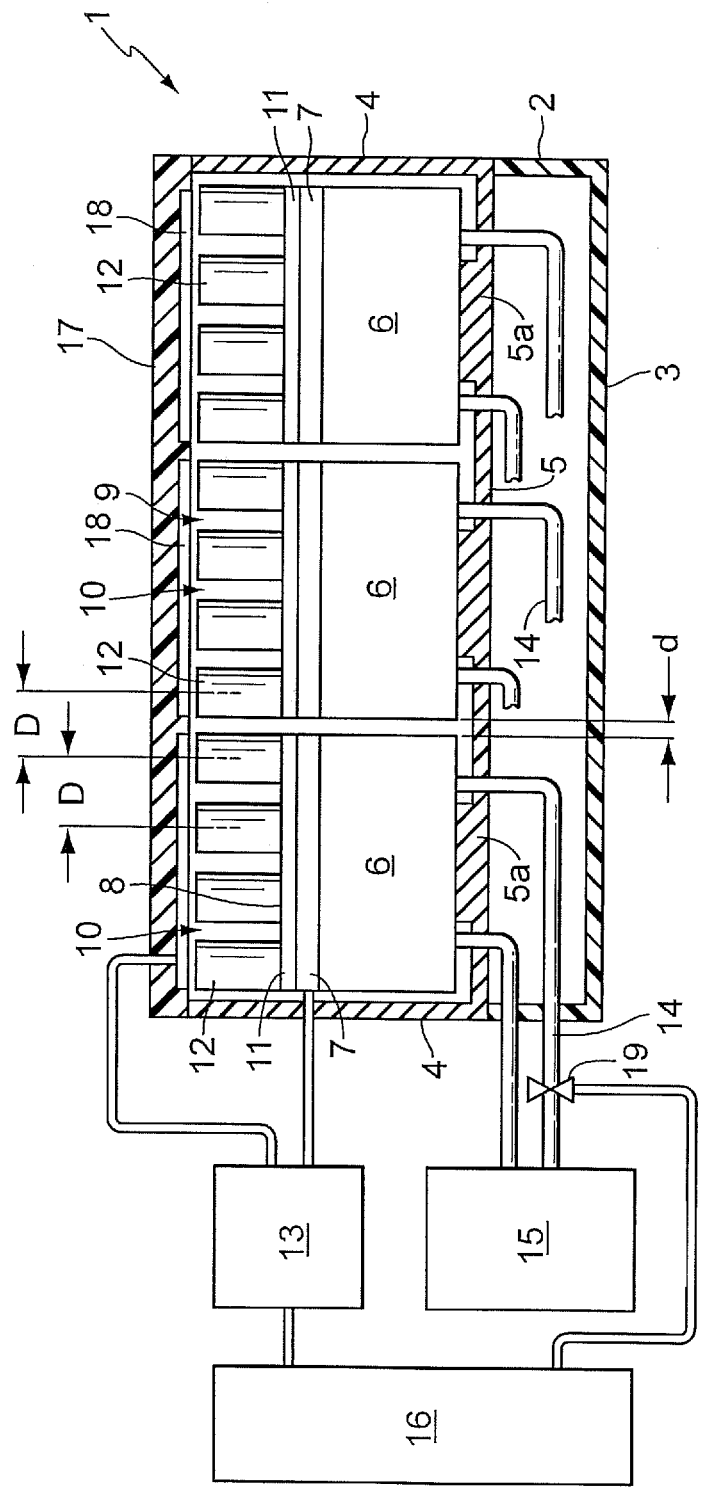
FIG. 1 depicts a section through a device according to the invention for carrying out chemical or biological reactions in accordance with an embodiment.

In the following description, reference is made to the accompanying drawings that form a part thereof, and in which are shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, not to be taken in a limited sense.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

As used herein, the terms "sample plate," "microtitration plate," "microtiter plate," and "microplate" are interchangeable and refer to a multi-welled sample receptacle for testing of chemical and biological samples. Microplates can have wells that are conical, cylindrical, rectilinear, tapered, and/or flat-bottomed in shape, and can be constructed of a single material or multiple materials. The microplate can conform to SBS Standards or it can be non-standard. Microplates can be open-faced (e.g. closed with a sealing film or caps) or close-chambered (e.g. microcard as described in U.S. Pat. No. 6,825,047). Open-faced microplates can be filled, for example, with pipettes (hand-held, robotic, etc.) or through-hole distribution plates. Close-chambered microplates can be filled, for example, through channels or by closing to form the chamber.

FIGS. 1 to 21 depict exemplary embodiments of methods and systems that include a reaction vessel receiving element divided into several segments, with the individual segments thermally decoupled and each segment assigned a heating element which may be actuated independently.

By this means the individual segments of the device may be set to different temperatures independently of one another. This makes it possible not only to set different temperature levels in the segments, but also for them to be held for varying lengths of time or altered at different rates of change. The device according to the invention thus permits optimization of all physical parameters critical for a PCR process, while the optimization process may be carried out on a single reaction vessel receiving element in which a microtiter plate may be inserted.

With the device according to the invention it is therefore also possible to optimise the residence times and rates of temperature change without having to distribute the reaction mixture over different microtiter plates for this purpose. Moreover, it is also possible to optimize the mixture volume by varying the mixture volume over different reaction vessel segments.

The thermocycling device according to the invention is in particular suitable for optimizing the multiplex PCR process, in which several different primers are used.

FIG. 1 shows a first embodiment of the device 1 according to the invention for carrying out chemical or biological reactions in a schematic sectional view.

The device has a housing 2 with a bottom 3 and side walls 4. Located just above and parallel to the bottom 3 is an intermediate wall 5, on which are formed several bases 5a. In the embodiment shown in FIG. 1, a total of six bases 5a are provided, arranged in two rows of three bases 5a each.

Mounted on each of the bases 5a is a heat exchanger 6, a Peltier element 7 and a segment 8 of a reaction vessel receiving element 9. The heat exchanger 6 is part of a cooling device and the Peltier element 7 is part of a combined heating and cooling device. The elements (heat exchanger, Peltier element, segment) mounted on the bases 5a are bonded by an adhesive resin with good heat conducting properties, so that good heat transfer is realized between these elements, and the elements are also firmly connected to a segment element 10. The device has altogether six such segment elements 10. Instead of adhesive resin, a heat conducting film or a heat conducting paste may also be provided.

Each of the segments 8 of the reaction vessel receiving element 9 has a base plate 11 on which tubular, thin-walled reaction vessel holders 12 are integrally formed. In the embodiment depicted in FIG. 1, in each case 4×4 reaction vessel holders 12 are arranged on a base plate 11. The distance d between adjacent segments 8 is such that the reaction vessel holders 12 of all segments S are arranged in a regular pattern with constant grid spacing D. The grid spacing D is chosen so that a standardised microtiter plate with its reaction vessels may be inserted in the reaction vessel holders 12. In various other embodiments, D is not a constant but varies to meet the desired application needs.

By providing the distance d between adjacent segments, an air gap which thermally decouples the segments 8 and segment elements 10 respectively is formed.

The reaction vessel holders 12 of the device shown in FIG. 1 form a grid with a total of 96 reaction vessel holders, arranged in eight rows each with twelve reaction vessel holders 12. One of ordinary skill in the art understands that embodiments including more or less than 96 reaction vessel holders are contemplated.

The Peltier elements 7 are each connected electrically to a first control unit 13. Each of the heat exchangers 6 is connected via a separate cooling circuit 14 to a second control unit 15. The cooling medium used is for example water, which is cooled in the cool temperature control unit before transfer to one of the heat exchangers 6.

The first control unit 13 and the second control unit 15 are connected to a central control unit 16 which controls the temperature cycles to be implemented in the device. Inserted in each cooling circuit 14 is a control valve 19, which is controlled by the central control unit 16 to open or close the respective cooling circuit 14.

Pivotably attached to the housing 2 is a cover 17 in which additional heating elements 18 in the form of Peltier elements, heating films or semiconductor heating elements may be located. The heating elements 18 form cover heating elements, each assigned to a segment 8 and separately connected to the first control unit 13, so that each heating element 18 may be individually actuated. In various embodiments, heating element 18 can be single or multiple heating elements that cover the all of the reaction vessel segments or overlap to cover several segments.

The mode of operation of the device according to the invention is explained in detail below.

There are three modes of operation.

In the first operating mode all segments are set to the same temperature, i.e., the same temperature cycles are run on all segments. This operating mode corresponds to the operation of a conventional thermocycling device.

In the second operating mode the segments are actuated with different temperatures, wherein the temperatures are so controlled that the temperature difference $\Delta T$ of adjacent segments 8 is less than a predetermined value K which amounts for example to 5°-15° C. The value to be chosen for K depends on the quality of the thermal decoupling. The better the thermal decoupling, the greater the value which can be chosen for K.

The temperature cycles input by the user may be distributed automatically by the central control unit 16 to the segments 8, so that the temperature differences between adjacent segments are kept as small as possible.

This second operating mode may be provided with a function by which the user inputs only a single temperature cycle or PCR cycle, and the central control unit 16 then varies this cycle automatically. The parameters to be varied, such as temperature, residence time, mixture volume, or rate of temperature change, may be chosen by the user separately or in combination. Variation of the parameters is effected either by linear or sigmoidal distribution.

In the third operating mode, only part of the segments is actuated. In plan view (FIG. 3, FIG. 4, FIGS. 6 to 9) the segments 8 have side edges 20. In this operating mode, the segments 8 adjacent to the side edges of an actuated segment 8 are not actuated. If the segments 8 themselves form a regular pattern (FIG. 3, FIG. 4, FIG. 6, FIG. 7 and FIG. 8), then the actuated segments are distributed in a chessboard pattern. In the embodiments shown in FIGS. 1 to 4, three of the six segments 8 can be actuated, namely the two outer segments of one row and the middle segment of the other row.

In this operating mode the actuated segments are not influenced by the other segments, and their temperature may be set completely independently of the other actuated segments. By this means it is possible to run quite different temperature cycles on the individual segments, with one of the segments for example heated up to the denaturing temperature and another held at the annealing temperature. Thus it is possible for the residence times, i.e. the intervals of time for which the denaturing temperature, the annealing temperature and the elongation temperature are held, also the rates of temperature change, to be set as desired, and run simultaneously on the individual segments. In this way it is possible to optimize not only the temperatures, but also the residence times, mixture volume, and the rates of temperature change.

In this operating mode it may be expedient to heat the non-actuated segments 8 a little, so that their temperature lies roughly in the range of the lowest temperature of the adjacent actuated segments. This avoids the non-actuated segments forming a heat sink for the actuated segments and affecting their temperature profile adversely.

Figure 2:
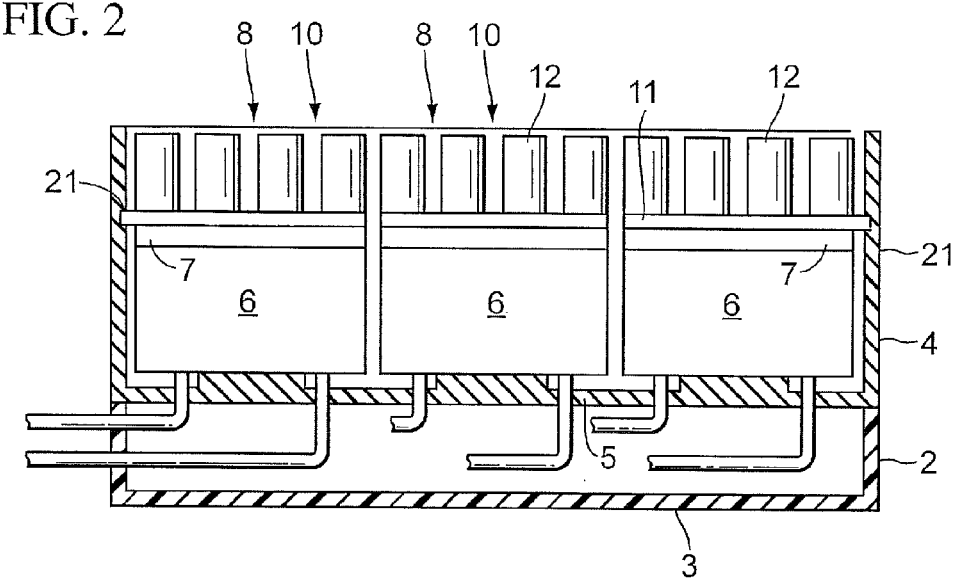
FIG. 2 depicts a section through an area of a device according to the invention for carrying out chemical or biological reactions in accordance with another embodiment.
Figure 3:
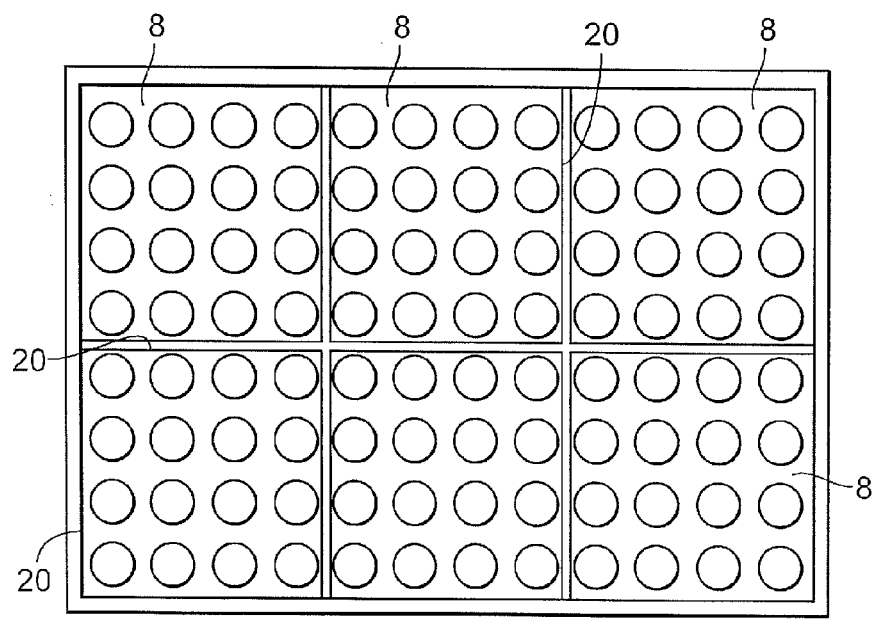
FIG. 3 depicts a schematic plan view of the device of FIG. 2.

A second embodiment of the device according to the invention is shown in FIGS. 2 and 3. The basic design corresponds to that of FIG. 1, so that identical parts have been given the same reference number.

The second embodiment differs from the first embodiment by virtue of the fact that the side edges 20 of the segments 8 adjacent to the side walls 4 of the housing 2 engage in a slot 21 running round the inner face of the side walls 4, and are fixed therein for example by bonding. By this means the individual segment elements 10 are fixed in space, thereby ensuring that despite the form of the gaps between the segment elements 10, all reaction vessel holders 12 are arranged in the pattern of the reaction vessels of a microtiter plate. The side walls 4 of the housing 2 are made of a non heat conducting material. This embodiment may also be modified such that the slot 21 is introduced in a frame formed separately from the housing 2. The frame and the segments inserted in it form a part which may be handled separately during production and is bonded to the heating and cooling devices.

Figure 4:
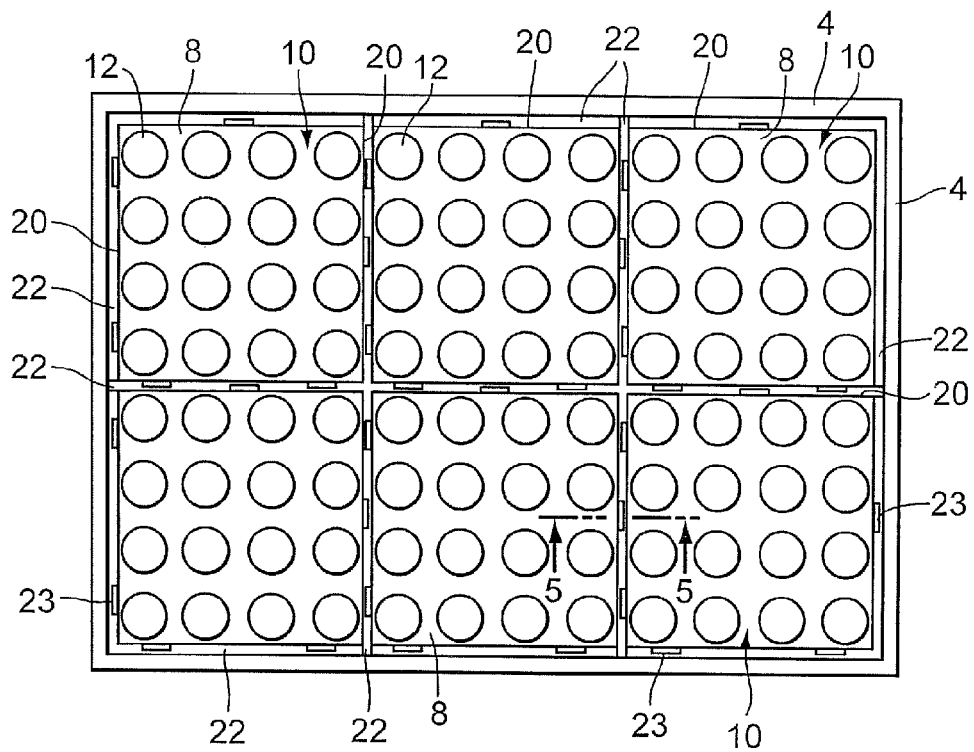
FIG. 4 depicts a schematic plan view of a device according to another embodiment.
Figure 5:
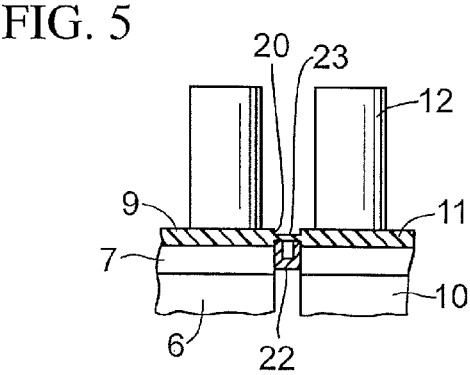
FIG. 5 an area of the device of FIG. 4 in a sectional view along the line A-A.

A third embodiment is shown schematically in FIGS. 4 and 5. In this embodiment, ties 22 of non heat conducting material are located somewhat below the base plates 11 of the segments 8 in the areas between the segment elements 10 and between the segment elements 10 and the side walls 4 of the housing 2. On the side edges 20 of the segments 8 and of the base plates 11 respectively are formed hook elements 23 which are bent downwards. These hook elements 23 engage in corresponding recesses of the ties 22 (FIG. 5), thereby fixing the segments 8 in their position. The hook elements 23 of adjacent segments 8 are offset relative to one another. The ties 22 thus form a grid, into each of the openings of which a segment 8 may be inserted.

This type of position fixing is very advantageous since the boundary areas between the segments 8 and the ties 22 are very small, so that heat transfer via the ties 22 is correspondingly low. Moreover this arrangement is easy to realise even in the confined space conditions between adjacent segment elements.

Shown in schematic plan view in FIGS. 6 to 9 are reaction vessel receiving elements 9 which represent further modifications of the device according to the invention. In these reaction vessel receiving elements 9, the individual segments 8 are joined by webs 24 of a thermally insulating material joined to form a single unit. The ties 22 are arranged between the side edges 20 of the base plates 11, to which they are fixed for example by bonding.

Figure 6:
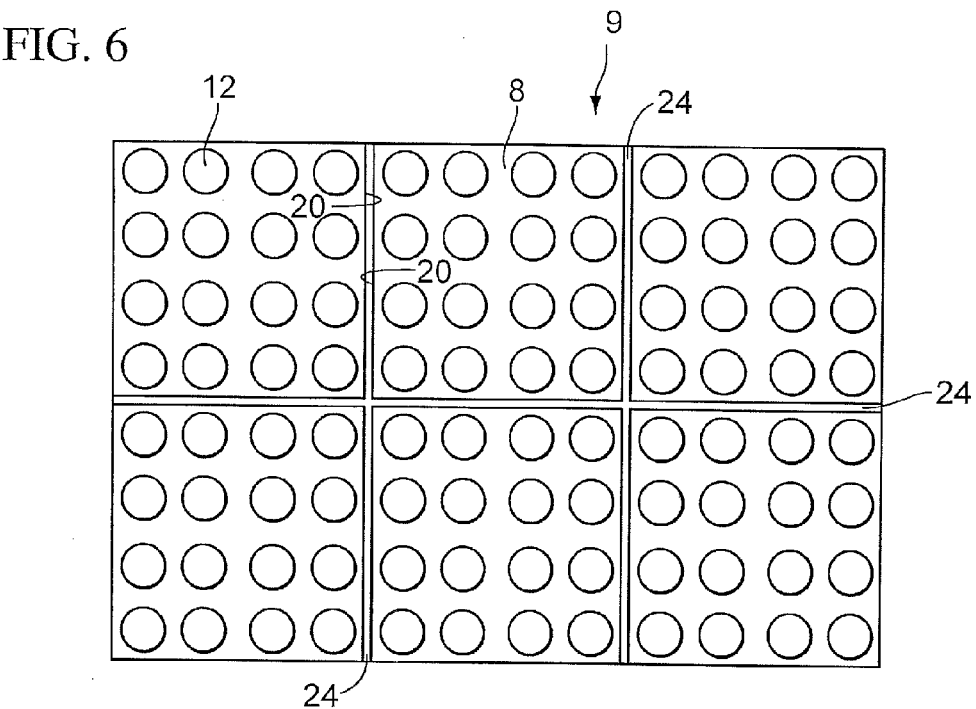
FIGS. 6 to 9 depict schematic plan views of reaction vessel receiving elements with differing segmentation.

The segmentation of the reaction vessel receiving element of FIG. 6 corresponds to that of the first and second embodiment (FIG. 1-3), in which 4×4 reaction vessel holders are arranged on each segment B.

Figure 7:
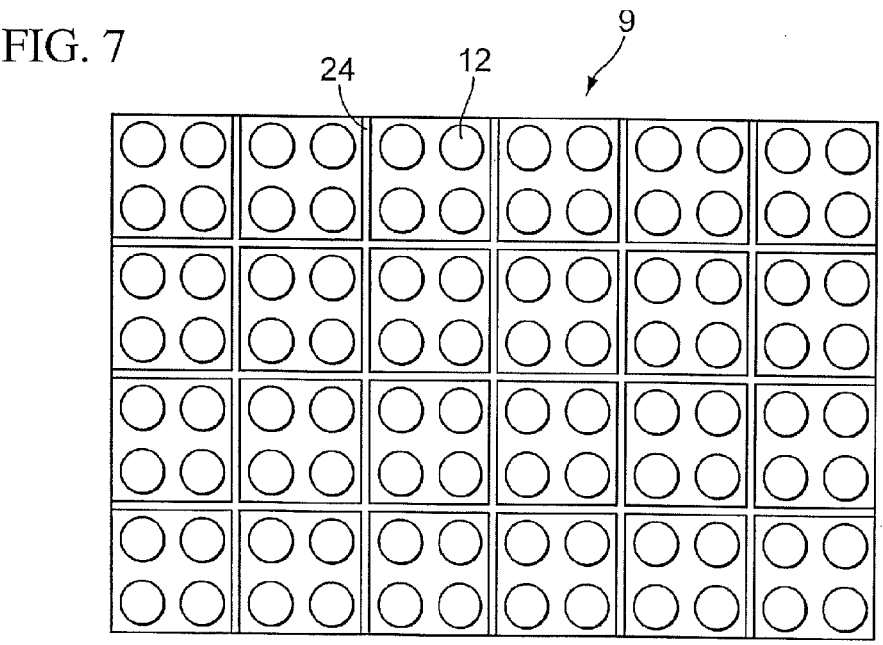

The reaction vessel receiving element 9 shown in FIG. 7 is comprised of 24 segments 8 each with 2×2 reaction vessel holders 12, while the segments 8 are in turn connected by means of thermally insulating webs 24.

Figure 8:
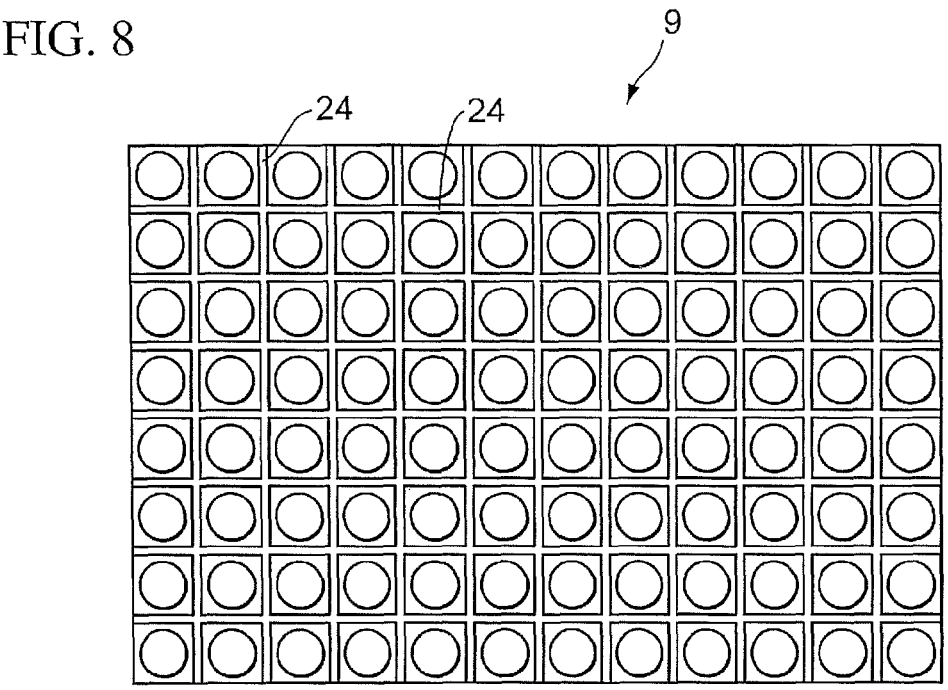

In the reaction vessel receiving element 9 shown in FIG. 8, each segment 8 has only a single reaction vessel holder 12.

For the relatively finely sub-divided reaction vessel receiving elements 9 it is expedient to integrate temperature sensors in the thermocycling device. These temperature sensors sense the temperatures of the individual segments, so that the temperature of the segments 8 is regulated in a closed control loop on the basis of the temperature values determined by the temperature sensors.

Infrared sensors may for example be used as temperature sensors, located e.g. in the cover. With this sensor arrangement it is possible to sense the temperature of the reaction mixture directly.

Figure 9:
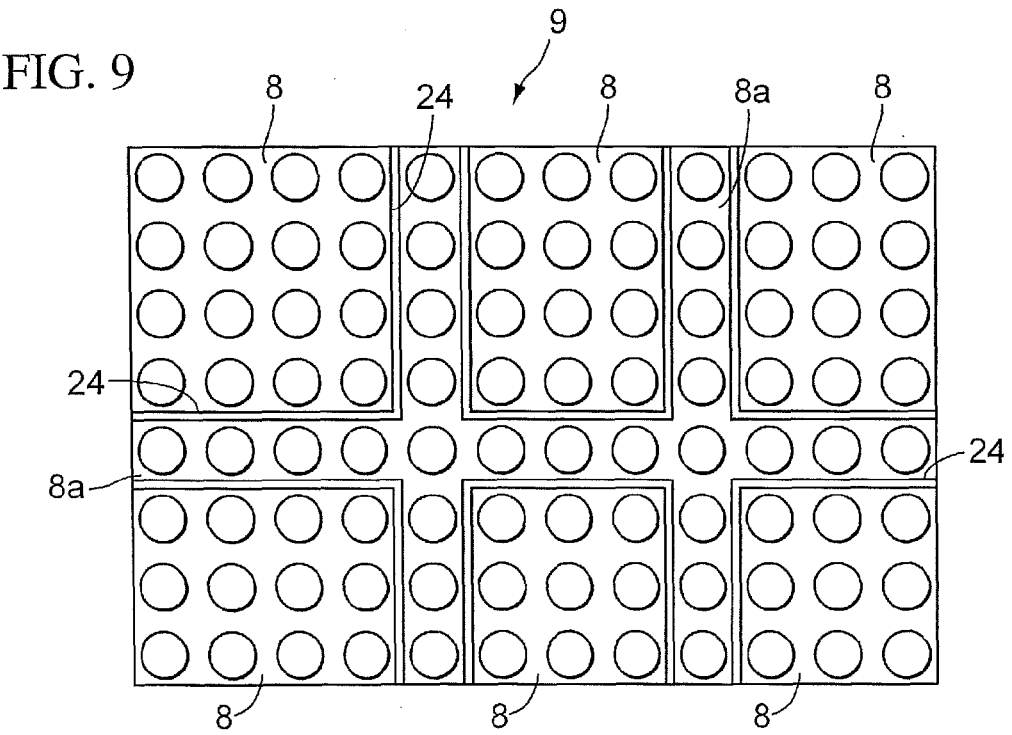

FIG. 9 shows a reaction vessel receiving element 9 with six segments 8, rectangular in plan view, and a segment 8a in the form of a double cross formed by three intersecting rows of reaction vessel holders 12. The six rectangular segments 8 are each separated from the next rectangular segment by a row or column of reaction vessel holders. This segmentation is especially advantageous for the third operating mode described above, since the rectangular segments 8 are not in contact with one another and may therefore be actuated simultaneously as desired, with only the segment 8a in the form of a double cross not being actuated.

The segments 8 of the reaction vessel receiving element 9 are made from a metal with good heat conducting properties, e.g. aluminium. The materials described above as non-heat conducting materials or thermally insulating materials are either plastics or ceramics.

Figure 10:
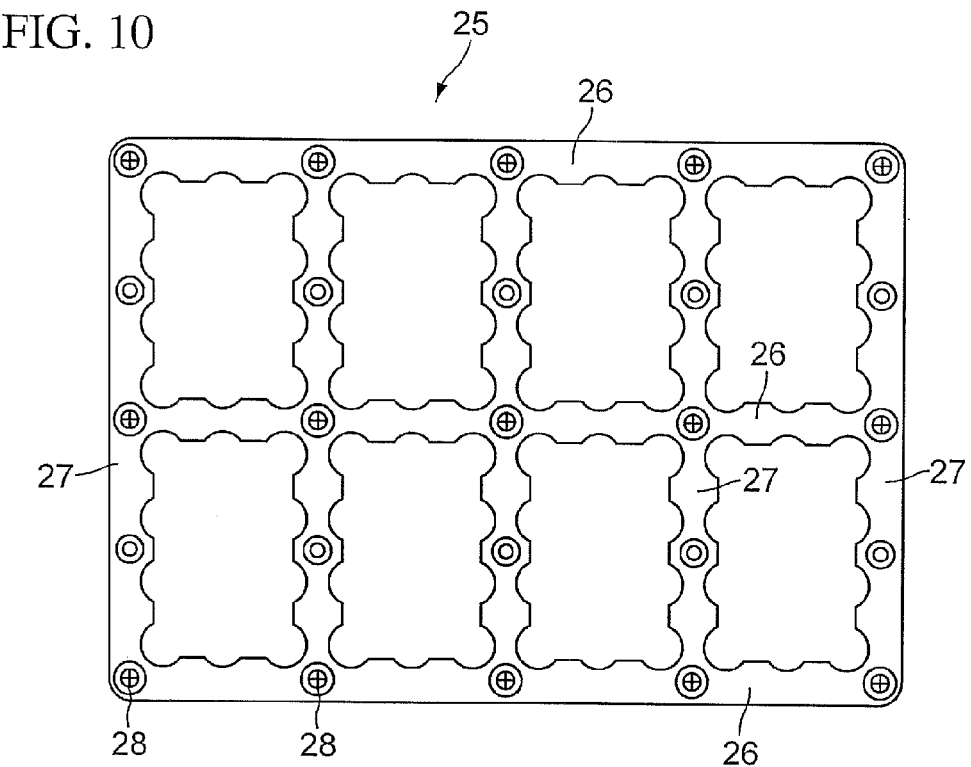
FIG. 10 depicts a clamping frame in plan view.
Figure 11:
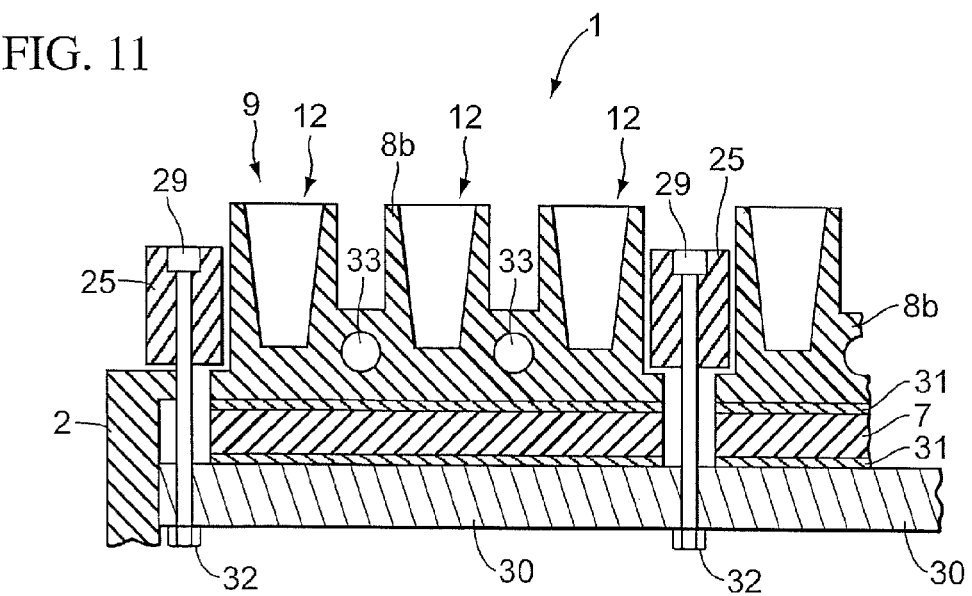
FIG. 11 depicts a device according to the invention in which segments of a reaction vessel receiving element are fixed by the clamping frame according to FIG. 10.

A further embodiment of the device according to the invention is shown in FIG. 11. In this embodiment the individual segments 8b of the reaction vessel receiving element 9 are fixed in position by means of a clamping frame 25 (FIG. 10).

The clamping frame 25 is grid-shaped and formed by longitudinal ties 26 and cross ties, wherein the ties 26, 27 span openings. Through these openings extend the reaction vessel holders 12 of the segments 8b. In the present embodiment, the ties 26, 27 are for instance in positive contact with the reaction vessel holders 12 and with the base plate 11 which protrudes from the reaction vessel holders. The 25 is provided with holes 28, through which pass bolts 29 for fixing the clamping frame to a thermocycling device 1.

Located below each of the segments 8b is a separately actuable Peltier element 7 and a cooling element 30 which extends over the area of all the segments 8b. Located in each case between the cooling element 30 and the Peltier element 7, and between the Peltier element 7 and the respective segment 8b is a heat conducting foil 31. The cooling element 30 is provided with holes through which extend the bolts 29, each fixed by a nut 32 to the side of the cooling element 30 facing away from the reaction vessel receiving element 9.

The clamping frame 25 is made from a non heat conducting material, in particular POM or polycarbonate. It therefore allows a fixing of the segments 8b of the reaction vessel receiving element 9 wherein the individual elements between the segments 8b and the cooling element 30 are under tension, thereby ensuring good heat transfer in the vertical direction between the individual elements. Since the clamping frame itself has poor heat conducting properties, the heat transfer between two adjacent segments 8b is kept low. For further reduction of heat transfer between two adjacent segments, the surfaces of the clamping frame 25 in contact with the segments 8b may be provided with narrow webs, so that in the areas adjoining the webs, air gaps are formed between the clamping frame 25 and the segments 8b.

In the embodiment shown in FIG. 11, a so-called heat pipe 33 is fitted between every two rows of reaction vessel holders 12. Such a heat pipe is distributed for example by the company THERMACORE INTERNATIONAL, Inc., USA. It is comprised of a gastight jacket, in which there is only a small amount of fluid. The pressure in the heat pipe is so low that the fluid is in a state of equilibrium between the liquid and the gaseous aggregate state, and consequently evaporates at a warmer section of the heat pipe and condenses at a cooler section. By this means, the temperature between the individual sections is equalised. The fluid used is, for example, water or freon.

Through integration of such a heat pipe in the segments 8b of the reaction vessel receiving element 9, a temperature equalisation is effected over the segment 8b. By this means it is ensured that the same temperature is present over the whole segment 8b.

Figure 12:
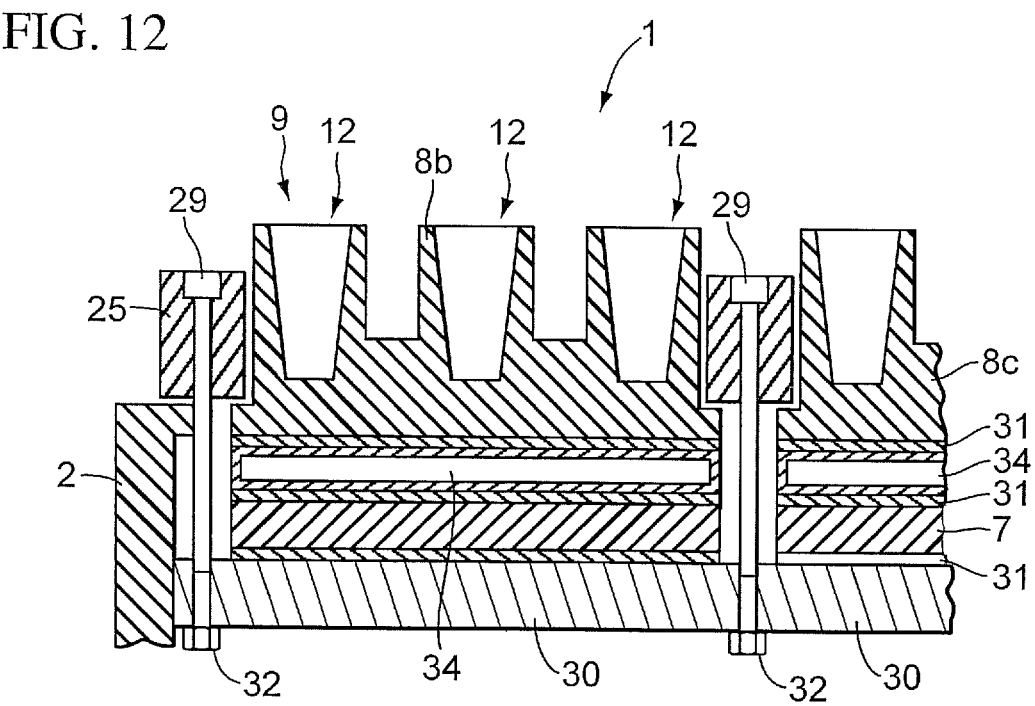
FIG. 12 depicts a further embodiment of a device according to the invention in section, in which segments of a reaction vessel receiving element are fixed by the clamping frame according to FIG. 10.

A further embodiment of the thermocycling device 1 according to the invention is shown in FIG. 12. The design of this thermocycling device is similar to that of FIG. 11, therefore similar parts have been given the same reference numbers.

The segments 8c of this thermocycling device 1, however, have no heat pipe. Instead of heat pipes, a temperature equalisation plate 34 is provided in the area beneath each of the segments 8c. These temperature equalisation plates 34 are flat elements with a surface corresponding to the basic surface of one of the segments 8c. These temperature equalisation plates 34 are hollow bodies with a small amount of fluid, and work on the same principle as the heat pipes. By this means it is once again ensured that there are no temperature variations within a segment 8c.

The temperature equalisation plate may however be made from materials with very good heat conducting properties, such as e.g. copper. Additional heating and/or cooling elements, e.g. heating foils, heating coils or Peltier elements, may be integrated in such a temperature equalisation plate. The heating and cooling elements support homogeneity and permit more rapid heating and/or cooling rates. A Peltier element, which generally does not have an even temperature distribution, is preferably combined with a flat heating element.

The reaction vessel receiving elements described above are comprised of a base plate with roughly tubular reaction vessel holders. Within the scope of the invention it is also possible to use a sample block, for example formed of metal, in which recesses to receive the reaction vessels of the microtiter plate are made.

Figure 13:
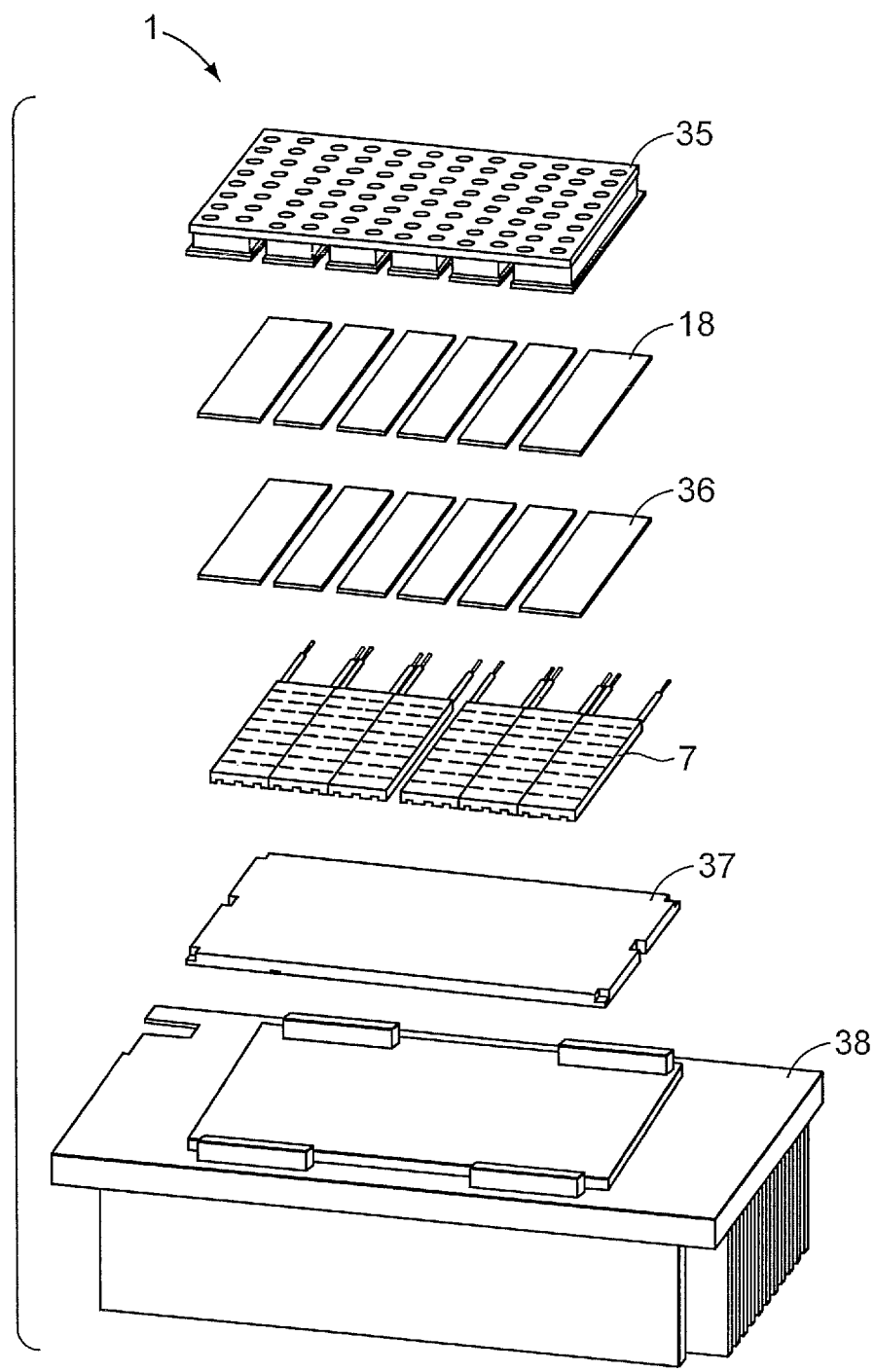
FIG. 13 depicts an exploded perspective view of a thermocycling device in accordance with the present teachings.
Figure 13A:
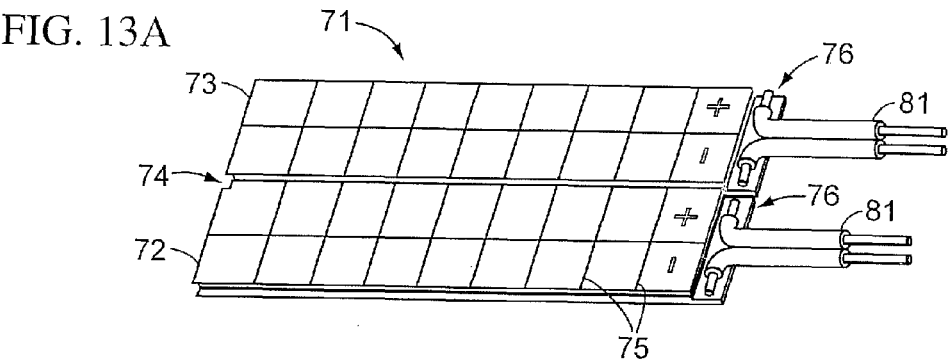
FIG. 13A depicts a perspective view of a TEC in accordance with the present teachings.
Figure 13B:
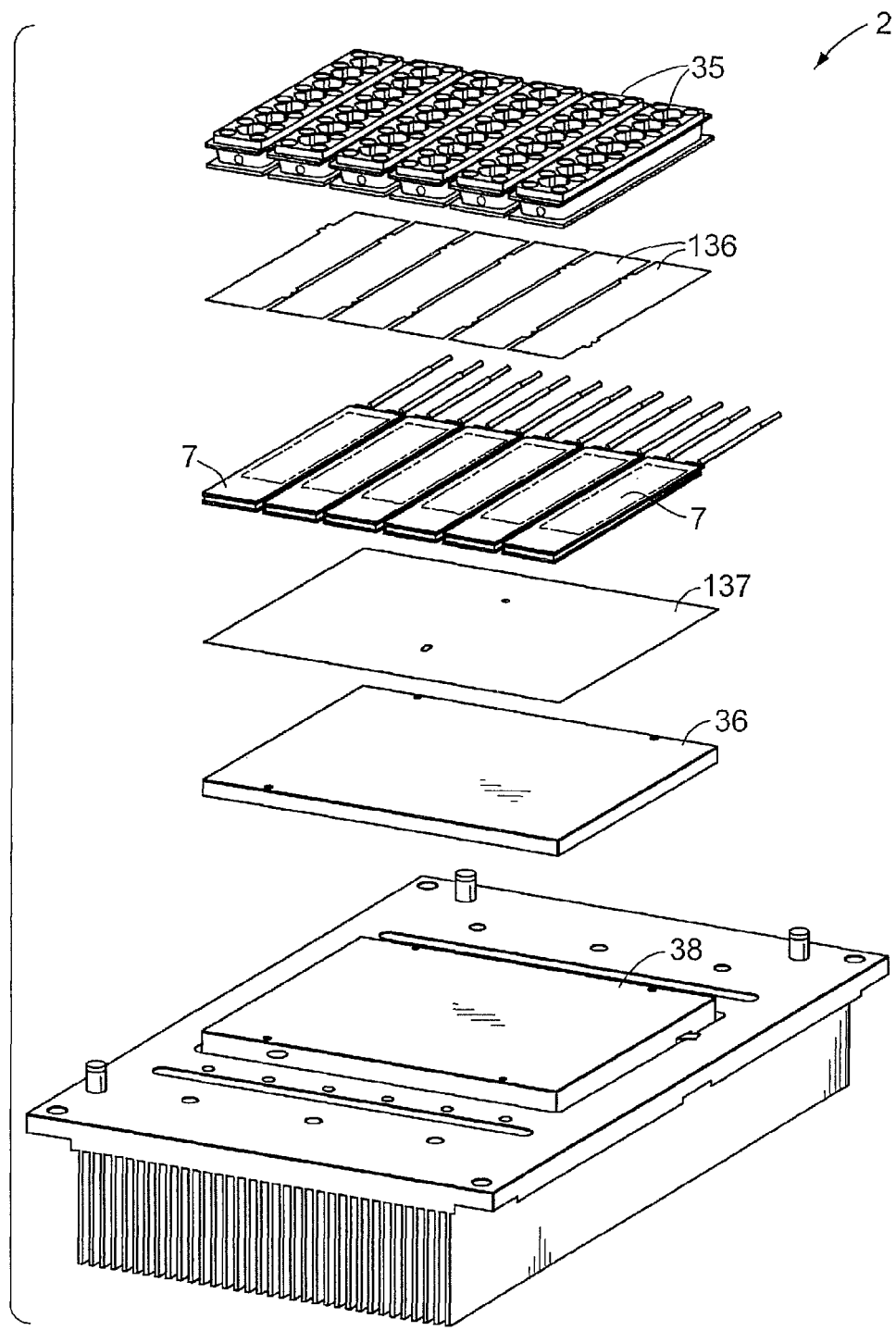
FIG. 13B depicts an exploded perspective view of another thermocycling device in accordance with the present teachings.
Figure 13C:
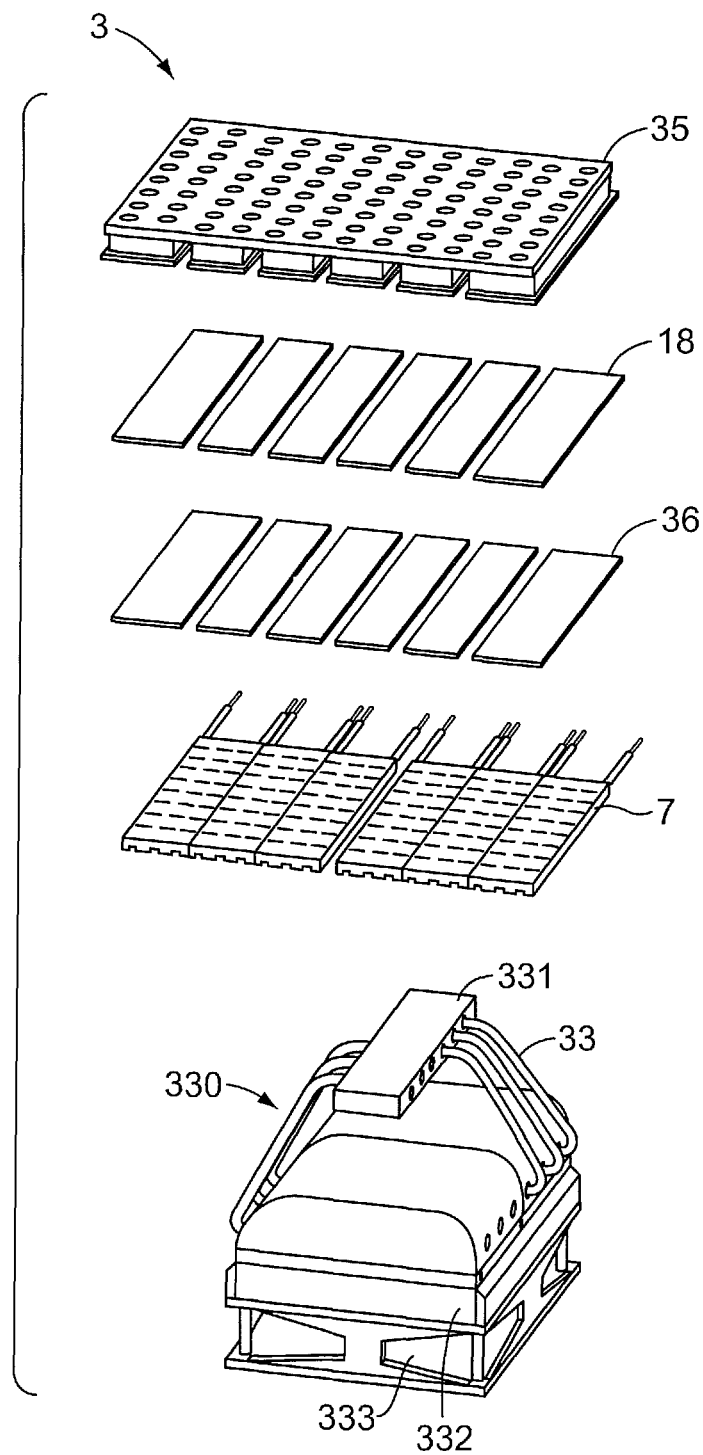
FIG. 13C depicts an exploded perspective view of another thermocycling device including a heat pipe cooler in accordance with the present teachings.
Figure 14D:
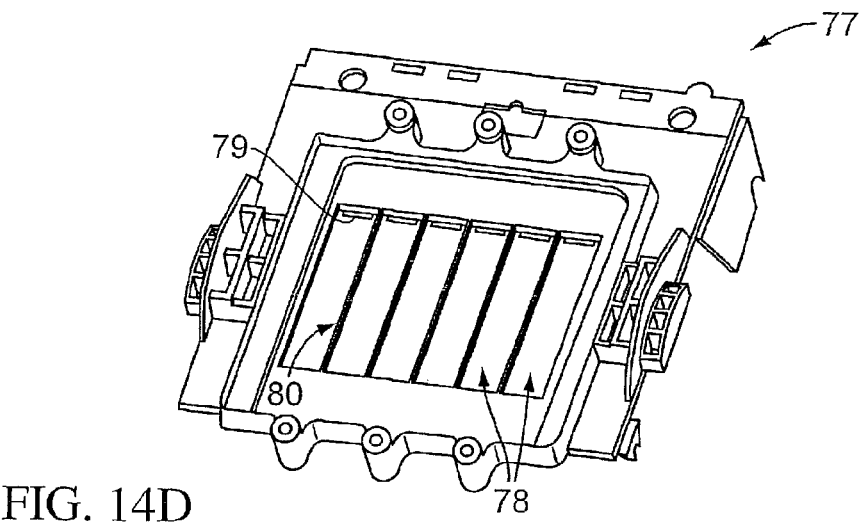
FIG. 14D depicts a perspective view of drip pan configured to secure a plurality of sample block segments in accordance with the present teachings.

FIGS. 13 and 13B are exploded perspective diagrams depicting exemplary thermocyclers for processing biological or chemical samples in accordance with the present teachings. Referring to FIG. 13, a thermocycler 1 can include a sample block 35, a plurality of heating elements 18 disposed adjacent to sample block 35, a plurality of thermoelectric cooling devices (TECs) 71 such as, for example, Peltier devices, and a plurality of temperature sensors (not shown). In various embodiments, a plurality of first metal plates 36 can be disposed between the plurality of heating elements 18 and plurality of TECs 7. A second metal plate 37 can also be disposed between plurality of TECs 7 and a heat sink 38.

Referring to FIG. 13B, another exemplary thermocycler is shown. A thermocycler 2, can include a sample block 35, a first thermal interface material 136 disposed adjacent to sample block 35, and a plurality of thermoelectric cooling devices (TECs) 7, such as, for example, Peltier devices disposed between first thermal interface material 136 and a second thermal interface material 137. Thermocycler 2 can further include a first metal plate 36, and a heatsink 38.

Sample block 35 can be formed of any material that exhibits good thermal conductivity including, but not limited to, metals, such as, aluminum, silver, gold, and copper, carbon or other conductive polymers. Sample block 35 can be configured to receive one microtiter plate. For example, the top of sample block 35 can include a plurality of recesses arranged in an array that correspond to the wells in the microtiter plate. For example, common microtiter plates can include 96 depressions arranged as an 8×12 array, 384 depressions arranged as a 16×24 array, and 48 depressions arranged as a 8×6 array or 16×3 array. Alternatively, the sample block can be flat or without recesses to mate with flat-bottomed wells of a microplate or a flat portion of the chambers of a microcard.

Figure 14A:
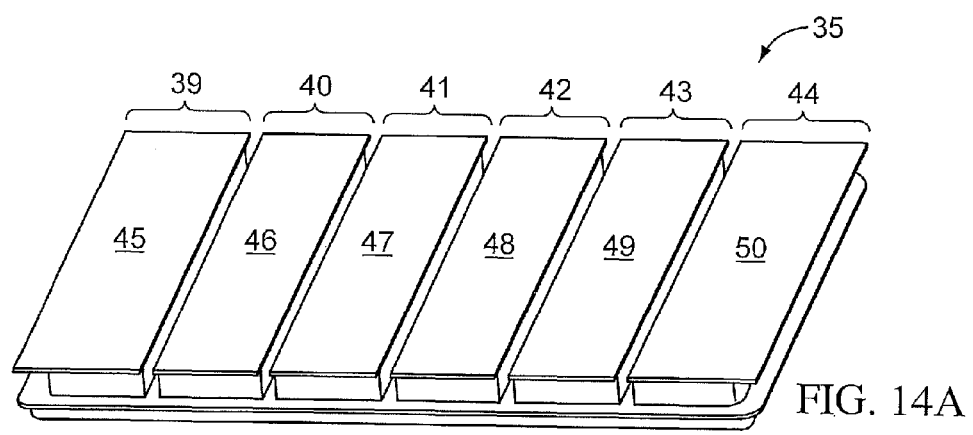
FIG. 14A depicts a perspective view of a sample block configured to define a plurality of zones in accordance with the present teachings.

Sample block 35 can be configured to define a plurality of zones. FIG. 14A shows a perspective view of the bottom of sample block 35 configured to define six zones 39-44. While the one piece top of sample block 35 can be configured to receive the microtiter plate, the bottom can be configured as six portions 45-50, where each bottom portion defines one of zones 39-44. Thus, each well in the top of sample block 351 would be included in one of zones 39-44. In the depicted embodiment, the top of sample plate 35 can receive a standard 96 well microplate, where the wells are configured in an 8×12 array. Each of the six zones 39-44, defined by the six bottom portions 45-50, would then include a 2×8 array of wells.

Figure 14B:
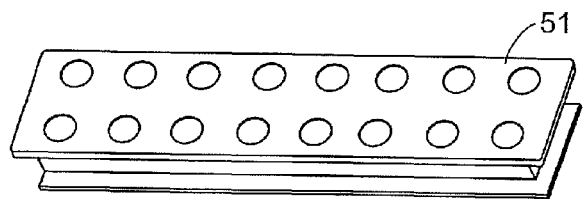
FIGS. 14B-C depict perspective views of sample block segments in accordance with the present teachings.

According to various embodiments, the sample block can comprise a plurality of separate sample block segments, where each segment defines a zone. FIG. 14B depicts a segment 51 that includes 16 wells. Six segments 51 can be used, for example, to form a sample block that receives one 96 well microtiter plate. Segments 51 can be positioned, for example, using a drip pan 77 shown in FIG. 14D. In various embodiments drip pan 77 can include a plurality of slots 78 and a plurality of bridges 80 to hold segments 51. Drip pan 77 can be formed of any suitable material including but not limited to a thermoplastic. Slots 78 can further include undercuts 79 to hold segments 51 in place. Seals (not shown) can also be disposed between undercut 79 and a flange on segments 51. Segments 51 can then be secured using, for example, screws. In this manner, heat flux from one zone to adjacent zones can be minimized and thermal uniformity at each zone can be provided. One of ordinary skill in the art understands that the disclosed sample blocks and drip pans are exemplary and that a sample block and/or drip pan can be configured to receive other standard microtiter plates, and be formed of less than six or more than six segments.

Figure 14C:
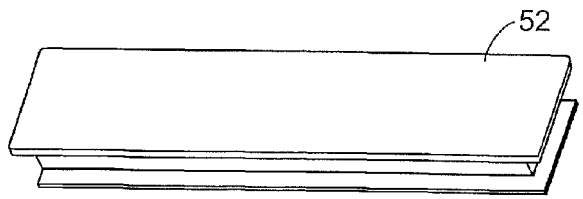

In various other embodiments, as shown in FIG. 14C, a sample block segment 52 can include a flat surface to accommodate a microcard format. The microcard format can include a flat-bottomed metallic foil that is segmented to thermally separate different chambers in the microcard.

Each zone can further include a heating element 18. Heating element 18 can be can be, for example, resistive heaters known to one of ordinary skill in the art and shaped, for example, as foils or loops to distribute heat uniformly across a zone. In other embodiments, heating element 18 can be a resistive ink heater or an adhesive backed heater, such as, for example, a Kapton heater.

In various embodiments, each zone can also include a first metal plate. As shown in FIG. 13, first metal plate 36 can be disposed between heating element 18 and TEC 7.

Each zone further includes a TEC, such as, for example, a Peltier device. The plurality of TECs 7 can be configured to correspond to the plurality of zones. For example, the plurality of TECs 7 can correspond to the six zones defined by sample block 35. According to various embodiments, TECs 7 can provide course heating to near a control temperature and the heating elements 18 can provide fine heating to about the control temperature. The TEC can provide all heating and cooling. As used herein, the term "control temperature" refers to any desired temperature that can be set by a user, such as, for example, temperatures for denaturing, annealing, and elongation during PCR reactions. Each of the plurality of TECs can function independently without affecting other of the plurality of TECs. This can provide improved temperature control at each of the zones.

In various other embodiments, TECs 7 can be integrated into a single unit. As shown in FIG. 13A, TEC 71 can be a two zone TEC including a first zone 72 and a second zone 73. First zone 72 and a second zone 73 can be separated by a gap 74, but, for example, share a common foundation. In various embodiments, electrical connections 81 of TECs 71 can be oriented in a direction opposite that of other electrical connections, such as, for example, the electrical connections of heating element 18. This can increase ease of routing the electrical connections and minimize interference between electrical connections. Each TEC zone can provide heating and/or cooling independently to different zones of the sample block. By integrating two or more TEC zones into a single unit, performance, alignment, and ease of assembly can be improved. In various embodiments, dicing can be used to improve the life of TEC. Dicing, depicted as lines 75, can also reduce the thermal stress the TEC and reduce the thermal stress on couplings 76. One of ordinary skill in the art understands that the depicted two zone TEC is exemplary and that more than two zones are contemplated.

In various embodiments, the thermocycler can further include second metal plate 37 disposed between TECs 7 and heatsink 38. In various embodiments, the segmented block can be cooled by a single TEC device and heated by individualized resistive heaters for each segment. Alternatively, the segmented block can be cooled by individualized TEC devices for each segment and heated by a single resistive heater.

Thermocycler 1 can be operated in at least three modes as disclosed above. In a first mode, each zone is set to the same temperature. In a second mode, each of the zones is actuated with a different temperature. And, in a third mode only some of the zones are utilized. In an exemplary method of operation, thermocycler 1 can process biological or chemical samples for PCR. Referring to FIGS. 13 and 14A, sample block 35 can define six zones 39-44. Zone 39-44 can be heated to a denaturing temperature $T_d$, in one of the three operating modes. In various embodiments, each zone can be heated to a different temperature, for example, where $T_{d1}$ is the denaturing temperature in zone 39, $T_{d2}$ is the denaturing temperature in zone 40, $T_{d3}$ is the denaturing temperature in zone 41, $T_{d4}$ is the denaturing temperature in zone 42, $T_{d5}$ is the denaturing temperature in zone 43, and $T_{d8}$ is the denaturing temperature in zone 44. For example, $T_{d2} \neq T_{d3}$ and $T_{d1} > T_{d2}$, or $T_{d1} \neq T_{d2}$ and $T_{d1} < T_{d2}$. The ramp rate to the denaturing temperatures $T_{d1-d6}$ and the residence time at $T_{d1-d6}$ can vary as desired. As shown in FIG. 13, TECs 7 can provide course heating to near a $T_{d1-d6}$ and the heating elements 18 can provide fine heating to about $T_{d1-d6}$.

Zones 39-44 can then be cooled to an annealing temperature $T_a$. In an embodiment, each zone can be cooled to a different temperature, for example, where $T_{a1}$ is the annealing temperature in zone 39, $T_{a2}$ is the annealing temperature in zone 40, $T_{a3}$ is the annealing temperature in zone 41, $T_{a4}$ is the annealing temperature in zone 42, $T_{a5}$ is the annealing temperature in zone 43, and $T_{a6}$ is the annealing temperature in zone 44. The ramp rate to the annealing temperatures $T_{a1-a6}$ and the residence time at $T_{e1-e6}$ can vary as desired.

During an elongating step, zones 39-44 can then be heated to an elongating temperature $T_e$. In an embodiment, each zone can be heated to a different temperature, for example, where $T_{e1}$ is the elongating temperature in zone 39, $T_{e2}$ is the elongating temperature in zone 40, $T_{e3}$ is the elongating temperature in zone 41, $T_{e4}$ is the elongating temperature in zone 42, $T_{e5}$ is the elongating temperature in zone 43, and $T_{e6}$ is the elongating temperature in zone 44. The ramp rate to the elongating temperatures $T_{a1-a6}$ and the residence time at $T_{a1-a6}$ can vary as desired. As shown in FIG. 13, TECs 7 can provide course heating to near a $T_{e1-e6}$ and the heating elements 18 can provide fine heating to about $T_{e1-e6}$.

The number of cycles, the mixture volumes, the steps of denaturing, annealing, and elongating, can also vary for each zone. For example, the samples in zone 39 can undergo a first number of cycles, such as, for example, fifty, while the samples in zone 40 can undergo a second number of cycles, such as, for example, one hundred. One of skill in the art will understand that the exemplary method is described with reference to a sample block configured to define six zones and that more than six or less than six zones can be used. In various other embodiments, the reaction vessel mixture volume can be filled with different volume at each zone 39-44 and each reaction vessel segment can be set according to the filled mixture volume for optimizing the PCR performance.

Figure 25A:
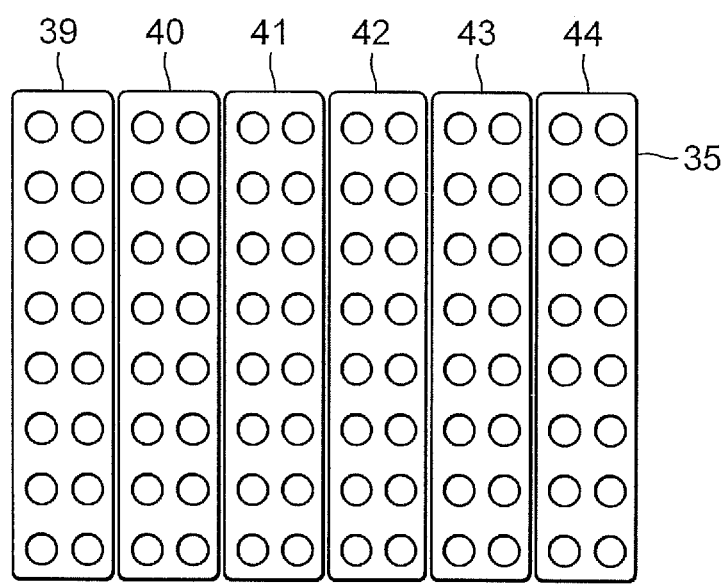
FIG. 25A depicts a top view of a thermal cycler including six zones for simultaneous zonal amplification of different targets in accordance with the present teachings.
Figure 25B:
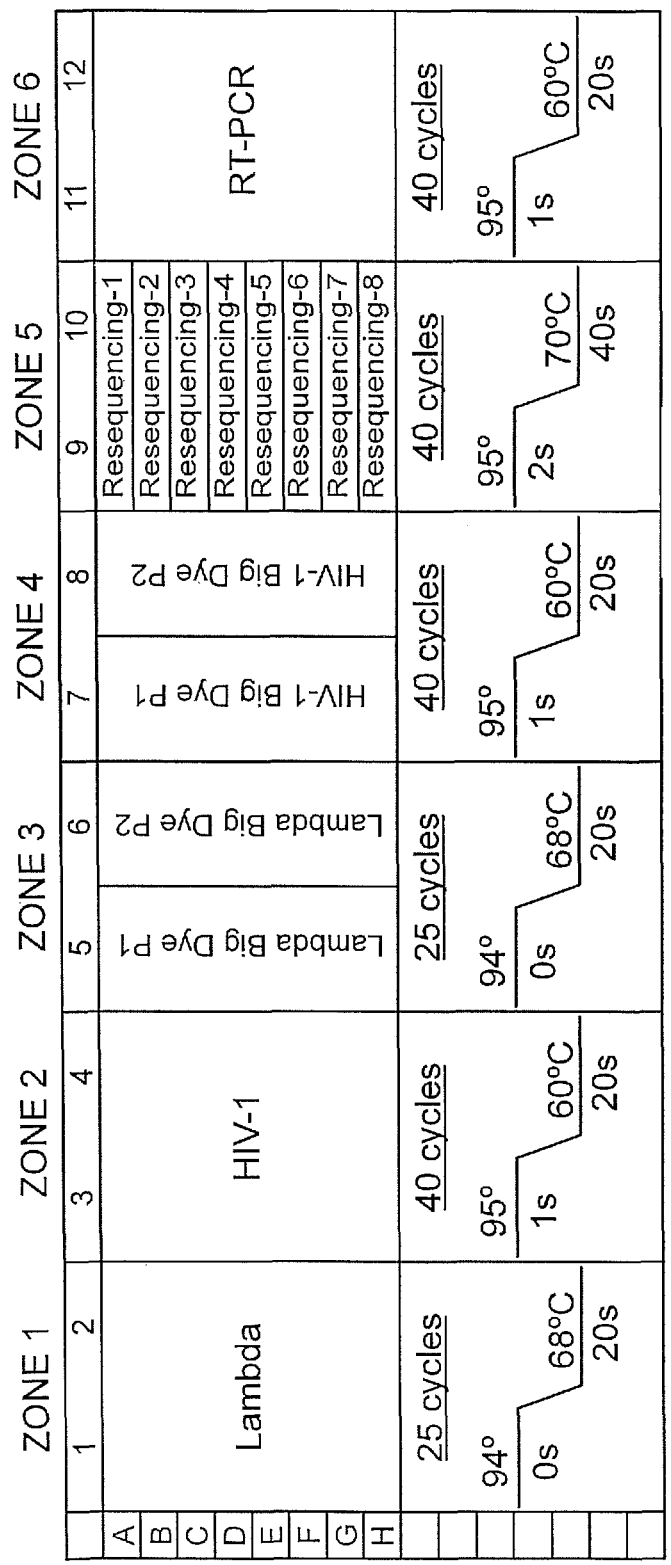
FIG. 25B is a chart depicting the denaturing step in six zones for simultaneous zonal amplification of different targets in accordance with the present teachings.

In accordance with other exemplary embodiments, the disclosed thermocyclers can be used for independent zonal amplification of different targets using different thermal and chemistry protocols during, for example, PCR. Referring to FIG. 25A, a top view of a thermal cycler 3 according to various embodiments of the present teachings is shown. Thermal cycler 3 can include a sample block 35 that is formed of a plurality of separate sample block segments 39-44. Alternatively, sample block 35 can be formed of a single segment. Sample block 35 can configured to include six zones (or portions). As shown in FIG. 25B, each of the six zones numbered 1 though 6 can include two columns (shown as columns 1-12) and 8 rows (shown as rows A-H) of wells. Although a 96 well sample plate with 16 wells in each segment is shown, one of ordinary skill in the art will understand that more or less wells can be included in each zone. One of ordinary skill in the art will also understand that six zones is exemplary and that more or less than six zones is contemplated.

According to various embodiments, multizone thermal cycler 3 can be used for independent zonal amplification of different targets by different thermal and chemistry protocols, where each zone is run simultaneously or with some overlap. Referring to FIG. 25B, sample block segments 39-44 can be used as six independent zones, shown as Zones 1-6. As an example, the zones were used to simultaneously amplify lambda DNA, HIV-1 DNA, and resequencing templates (Zones 1-2, and 5, respectively); Big Dye® cycle Sequencing of lambda and HIV-1 templates (Zones 3-4, respectively); and reverse transcriptase PCR of 18S rRNA (Zone 6) on a single 96-well plate. The PCR thermal protocol of lambda DNA primers in Zone 1, shown in FIG. 25B, included 25 cycles at an initial temperature up to 94° C., cooling to 68° C., and holding 20 seconds for 0.1 ng/uL lambda template, 0.2 uM of two primers, PCR master mix and water. The PCR thermal protocol of HIV-1 in Zone 2 included 40 cycles at an initial temperature of 95° C., holding 1 second, cooling to 60° C., and holding 20 seconds for 10 copies of HIV-1 template, 0.5 uM of two primers, PCR master mix, and water. Similarly, the PCR thermal protocol for primers used for resequencing in Zone 5 included 40 cycles at an initial temperature of 95° C., holding 2 seconds, cooling to 70° C., and holding 40 seconds for 10 ng/uL of human gDNA with 600 nM for each of the eight primers, master mix, and water. Further, Big Dye® Cycle Sequencing of lambda templates in Zone 3 included a PCR thermal protocol of 25 cycles at an initial temperature up to 94° C., cooling to 68° C., and holding 20 seconds for 3.2 pmol/uL of HIV-1 primer, 4 ng/uL of template, Big Dye® Terminator, and water. Big Dye® Cycle Sequencing of HIV-1 templates in Zone 4 included a PCR thermal protocol of 40 cycles at an initial temperature of 95° C., holding 1 second, cooling to 60° C., and holding 20 seconds for 3.2 pmol/uL of HIV-1 primer, 8 ng/uL of template, Big Dye® Terminator, and water. Reverse transcriptase PCR of 18S rRNA in Zone 6 included a PCR thermal protocol of 40 cycles at an initial temperature of 95° C., holding 1 second, cooling to 60° C., and holding 20 seconds for 10 uM of ribosomal forward primers and reverse primers, 40 uM of ribosomal dye probe, 50 ng/uL of template, master mix, MULV-RT/Rnase Inhibitor mix, and water. The results show that both exponential amplification of PCR and linear amplification of cycle sequencing can be performed in different zones of samples in a single microtiter plate positioned into a block with six segments. In various embodiments, PCR with different thermal protocols can be performed in adjoining zones, for example, normal PCR vs. touch-down PCR, two-step PCR vs. three-step PCR, normal PCR vs. fast PCR, etc. It will be appreciated by those skilled in the art of nucleic acid analysis that any number of temperature dependent reactions can be performed according to the present teachings. Illustrative examples of PCR, for example, can be found in Sambrook et al., Molecular Cloning, $3^{rd}$ Edition.

According to various embodiments, sample block 35 can be configured to define a plurality of zones in which the zones have different shapes. Referring to the exploded perspective view of FIG. 15, sample block 35 can be configured to define a first zone that includes wells near each edge of sample block 35 and a second zone that includes wells away from each edge of sample block 35. For example, a first TEC 53 can heat and cool the first zone and a second TEC 54 can heat and cool the second zone. In one embodiment, no heating elements are used. In this configuration, heat losses at corners and/or edges can be compensated for, or eliminated, without heating elements. Further, heat stored during heating can be compensated for, or eliminated, during cooling. In various other embodiments, heating elements (not shown) can be used. In this embodiment, first TEC 53 and second TEC 54 can provide course heating of the first zone and the second zone, respectively, to near the control temperature or temperatures while the heating elements can provide fine heating of the first and second zones to about the control temperature or temperatures. According to various other embodiments, sample block 35 can be formed of a plurality of segments, as shown in FIG. 14B, in which the segments correspond in shape to the plurality of zones. In various embodiments, the concentric zones described in FIG. 15 as rectangular TEC can be also be circular. For example, the segments can be circular forming a round block with circular TECs and the segments can be concentric or arced to fit a single round microtiter plate or other circular plastic sample holder.

Figure 16:
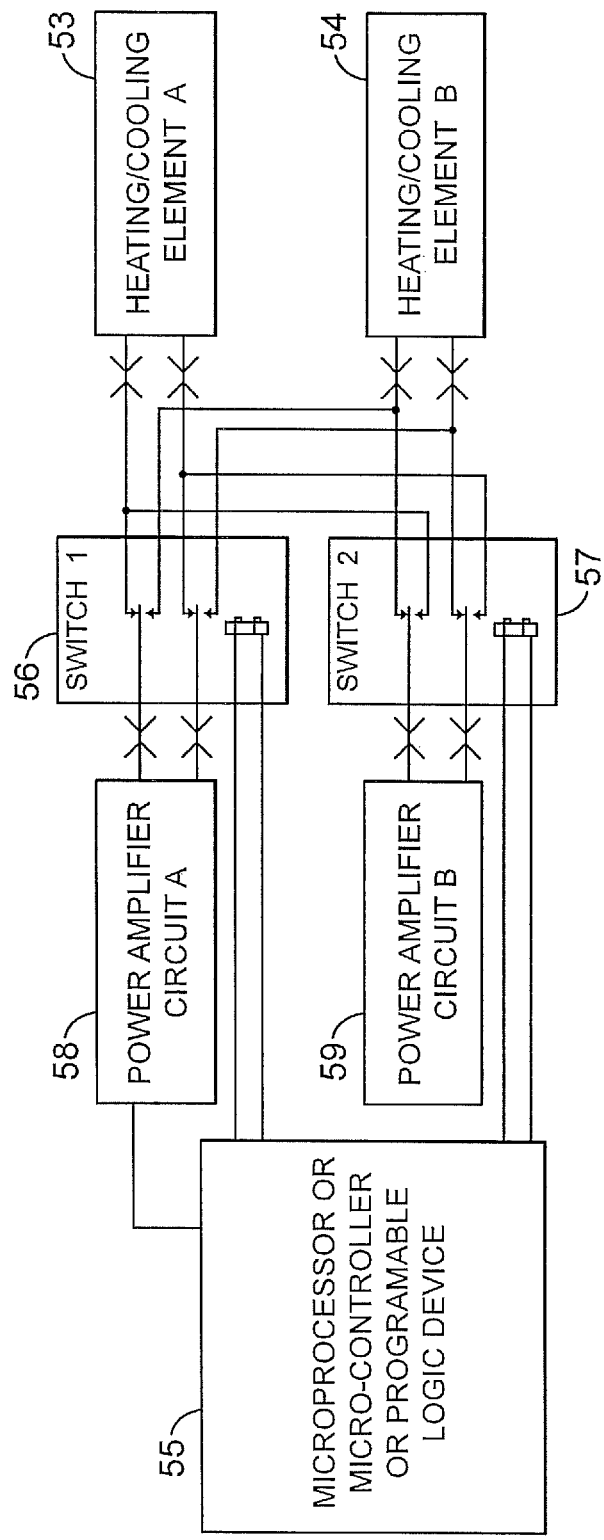
FIG. 16 schematically depicts multiple switches directing current from multiple power amplifiers to heating/cooling elements in accordance with the present teachings.

In various embodiments, multiple power amplifiers can be used to provide current to the TECs to heat and/or cool the multiple zones of the sample block. Referring to FIG. 16, a controller 55 can control a first switch 56 and a second switch 57 to direct current flow from a first power amplifier 58 and a second power amplifier 59 to one or both of first TEC 53 and second TEC 54. First switch 56 and second switch 57 can be, for example, relay switches, MOSFETS, transistors, IGBTs, or multiplexer devices. Controller 55 can be, for example, a microprocessor or programmable logic device. One of ordinary skill in the art will understand that the switches can direct current flow to and from the power amplifiers.

In operation, first switch 56 and second switch 57 can direct current flow from any power amplifier to any TEC. For example, first switch 56 and second switch 57 can direct current flow from first power amplifier 58 to first TEC 53 to heat and/or cool the first zone, and from second power amplifier 59 to second TEC 54 to heat and/or cool the second zone. Alternatively, first switch 56 and second switch 57 can direct current flow, for example, from first power amplifier 58 and from second power amplifier 59 to first TEC 53 to heat and/or cool the first zone. Similarly, first switch 56 and second switch 57 can direct current flow, for example, from first power amplifier 58 and from second power amplifier 59 to second TEC 54 to heat and/or cool the second zone. In this manner, the ramp rate to control the temperature in each of the plurality of zones can be increased or varied as desired. Although two switches and two power amplifiers are depicted, one of ordinary skill in the art will understand that more than two switches and power amplifiers can be used.

Figure 17:
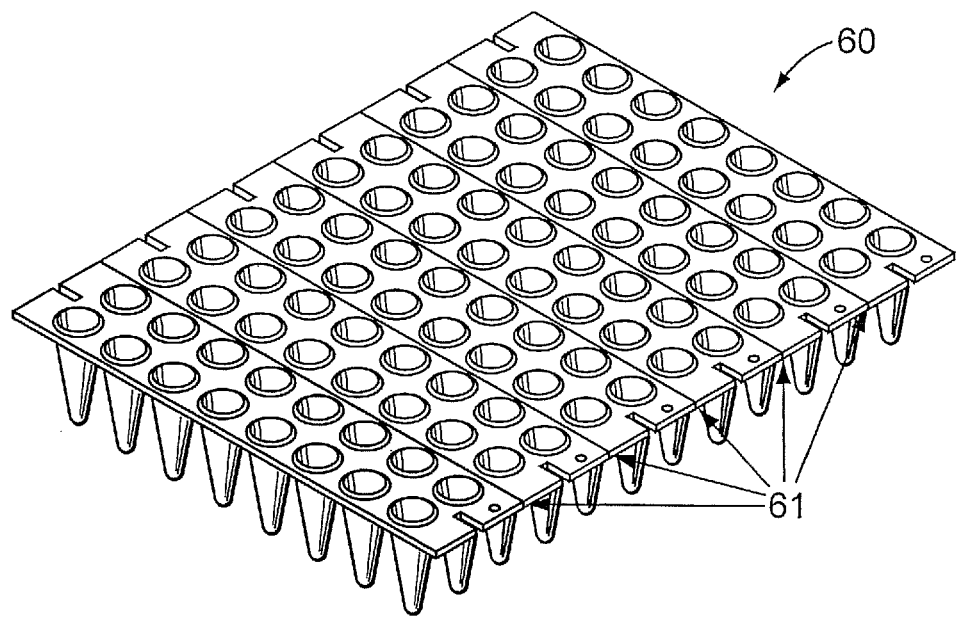
FIG. 17 depicts a perspective view of a microtiter plate in accordance with the present teachings.
Figure 18:
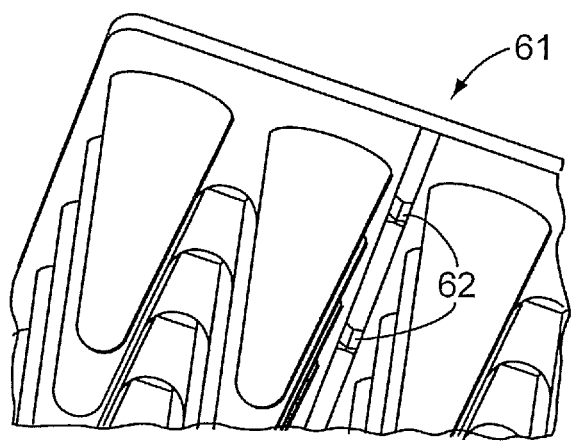
FIG. 18 depicts a perspective view of a slot in a microtiter plate in accordance with the present teachings.

In various other embodiments, a system for processing biological or chemical samples can further include a thermocycler and a detachable microtiter plate configured to detach into a plurality of segments that correspond to the plurality of zones. The detached microtiter segments can correspond, for example, to the plurality of zones defined by sample plate 35. FIG. 17 shows a perspective view of a detachable microtiter plate 60 comprising a plurality of slots 61. Slots 61 can be disposed between columns (or rows) of wells as needed. Detachable microtiter plate 60 can be separated into six pieces, each piece corresponding to one zone of, for example, sample block 35. FIG. 18 shows an enlarged view of one slot 61 including a plurality of breakaway tabs 62. In various embodiments, a rigid and brittle material can be used to form breakaway tabs 62 to facilitate separation by bending or cutting. One of skill in the art will understand that the disclosed embodiment is exemplary and that detachable microplate 60 can be configured to separate into less than six or more than six pieces as desired.

Figure 19:
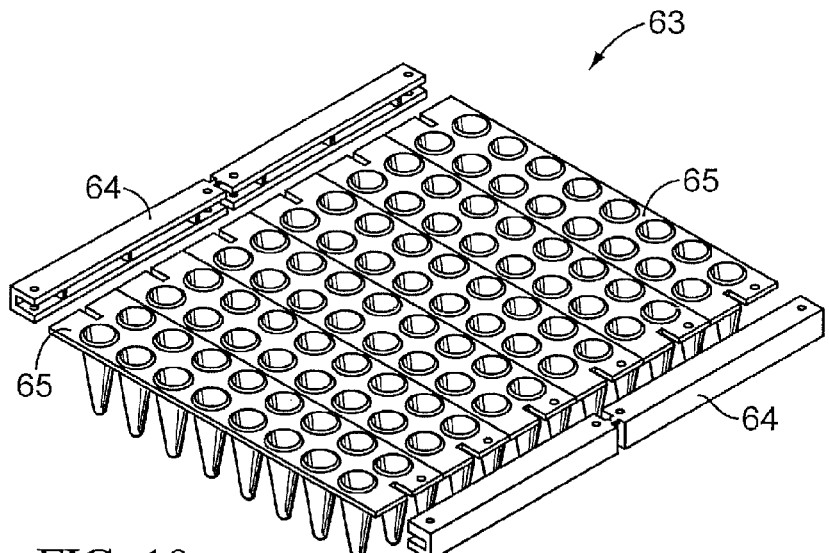
FIG. 19 depicts a perspective view of a modular microtiter plate in accordance with the present teachings.

In various embodiments, the microtiter plate can be modular to provide flexibility to the user. FIG. 19 is a perspective view of a modular microtiter plate 63 that includes microtiter plate holders 64 and a plurality of microtiter plate segments 65. As shown, two microtiter plate holders 64 can hold six microtiter plate segments 65 to form a standard 96 well microtiter plate. One of ordinary skill in the art will understand that the disclosed embodiment is exemplary and that less than six or more than six modular microtiter plates can be used to form a standard microtiter plate.

Figure 20:
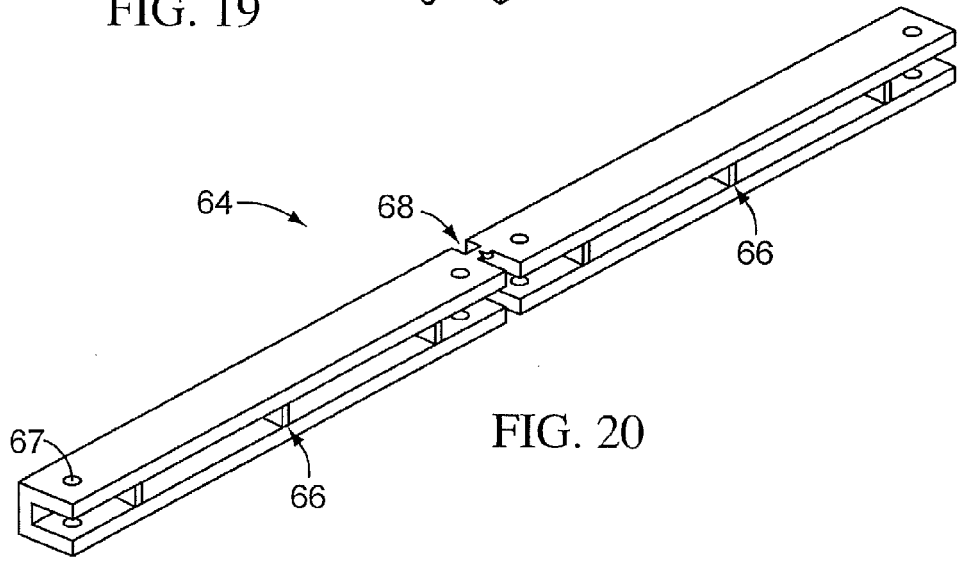
FIG. 20 depicts a perspective view of a modular microtiter plate holder in accordance with the present teachings.

FIG. 20 shows a perspective view of microtiter plate holder 64. In various embodiments, microtiter plate holder 64 can include a locating key 66, a locking feature 67, and/or a breakable joint 68. One or more locating keys 66, for example, can be placed along microtiter plate holder 64 to position microtiter plate segments 65. In an exemplary embodiment, locating key 66 can be a protrusion whose shape matches a locating slot in microtiter plate segment 65. One or more locking feature 67 can also be placed along microtiter plate holder 64 to secure the position of microtiter plate segments 65. In an exemplary embodiment, locking feature 67 can be, for example, a protrusion that fits into a locking hole in microtiter plate segment 65. Microtiter plate holder 64 can further include one or more breakable joints 68. Breakable joints 68 can allow microtiter plate holder 64 to be broken up into smaller pieces to hold one or more microtiter segments 65. In other words, after breakable joints 68 are broken, the one or more microtiter segments 65 held by the broken microtiter plate holders form less than a standard 96 well microtiter plate.

Figure 21:
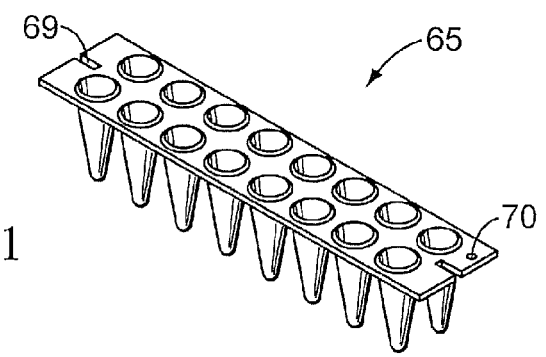
FIG. 21 depicts a perspective view of a microtiter plate segment in accordance with the present teachings.

FIG. 21 shows a perspective view of microtiter segment 65 including a key slot 69. One or more key slots 69 can be disposed on microtiter segment 65 to match a position of locating key 66 on microtiter plate holder 64. The shape of the one or more key slots 69 can further be configured to accept locating keys 66. Microtiter segment 65 can also include one or more locking holes 70 disposed to match a position of locking feature 67 on microtiter plate holder 64. The shape of the one or more locking holes can be configured to accept locking feature 67.

Figure 15:
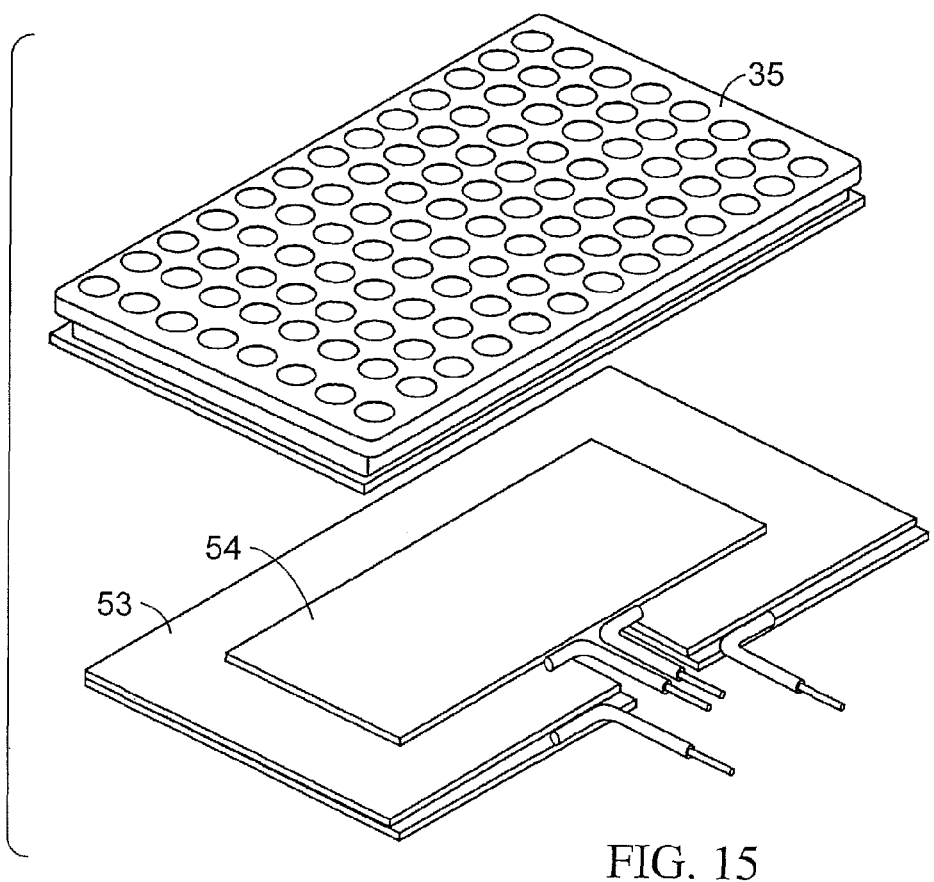
FIG. 15 depicts a perspective view of exemplary zones in accordance with the present teachings.
Figure 22:
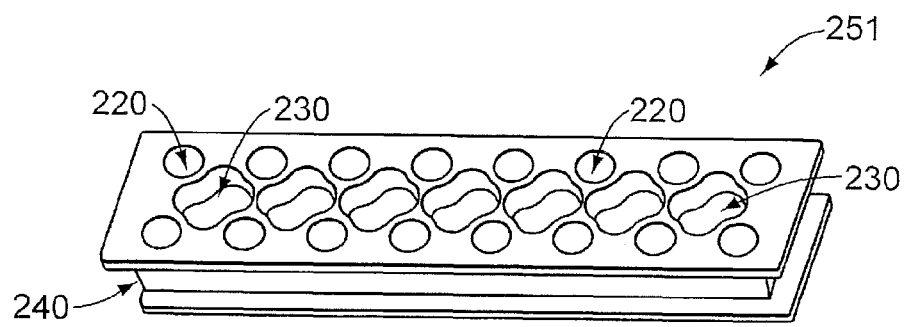
FIG. 22 depicts a machined sample block segment in accordance with the present teachings.

According to various embodiments, sample blocks 35 and sample block segments 51 and 52, as shown in FIGS. 13 through 15, can be machined from a solid piece of metal, formed by coupling several pieces of metal together, or formed by electroforming. FIG. 22 shows a machined sample block segment 251 that includes well-bores 220 to form the recesses for wells that can contain samples for thermal cycling. Mass-reduction bores 230 remove mass from the block to reduce the thermal mass of sample block segment 251. The sides 240 can be machined to reduce the mass on the sides dimensions of the block.

Sample blocks and sample block segments can also be formed by metal injection molding (MIM). MIM can combine the design freedom of plastic injection molding with the performance of metal. MIM can be used with metals such as aluminum, copper, tungsten, and alloys thereof. In various embodiments, MIM can include feedstock mixing wherein very small powders are mixed with a thermoplastic polymer (known as a binder) to form a precise mixture of ingredients that is pelletized and directly fed into a plastic molding machine. This pelletized powder-polymer is known as feedstock. The metal powder and binders can be mixed and heated in a mixer and cooled to form granulated feedstock. MIM can further include injection molding, wherein the feedstock is heated to melt the plastic and then with pressure is forced into a mold to form the desired geometry. The molded part is known as the "green" part. MIM can further include de-binding, wherein the polymer or binder is removed thermally by heating the "green" part to about 400° C. (or about 752° F.). While retaining its shape and size, the de-bound or "brown" part is a powder skeleton that is very brittle and porous. De-binding can be performed in an oven where heat and air flow are fluxed in and exhaust products are fluxed out. The oven converts the "green" part to the "brown" part. MIM can further include sintering, wherein the "brown" part is heated to more than 1200° C. allowing densification and shrinking of the powder into a dense solid with the elimination of pores. Sintering can be performed in an over where heat, hydrogen gas, and argon gas are fluxed in. Usually the sintering density is similar to a casting at about 98% of theoretical. The end result is the molded thermal part, e.g, the sample block.

In various embodiments, MIM can provide sample blocks with sizes of about 100 millimeters by about 100 millimeters. A typical 9-well sample block has larger dimensions. However, several sample block segments can be constructed by MIM to provide thermal cycling for a 96-well or 384-well microplate as described in European Pat. No. 1216098.

Figures 23A, 23B:
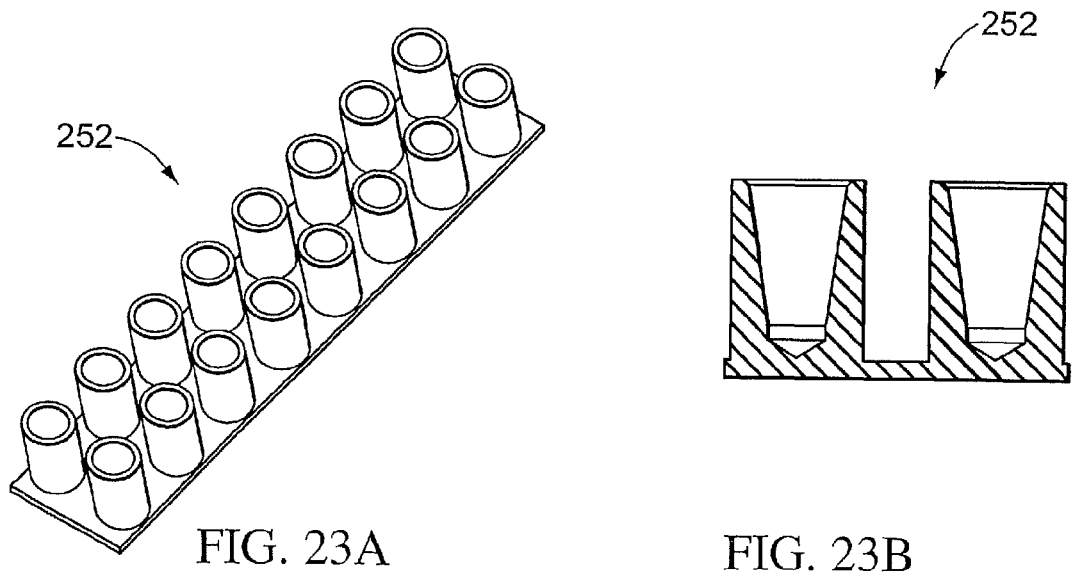
FIGS. 23A-23B depict sample block segments formed by metal injection molding in accordance with the present teachings.

Referring to FIGS. 23A and 23B, sample block segment 252 can provide low thermal mass with minimum attachment points to each section encircling the sample well and minimizing the thickness of the wall in sections around the sample well. As illustrated in FIG. 23B, sample block segment 252 can provide different configurations configured to contain sample wells with reactions volumes ranging from about 5.0 microliters to about 100 microliters. One of ordinary skill in the art will understand that other configurations are envisioned that, for example, correspond to microplate configurations known in the art. In various embodiments, the sample block material can be copper, aluminum, or silver. Chart 1 below shows a comparison of the sample blocks and sample block segments described herein demonstrating the differences in temperature ramp rate in degrees Celsius per second for different materials.

CHART 1

Figure 24:
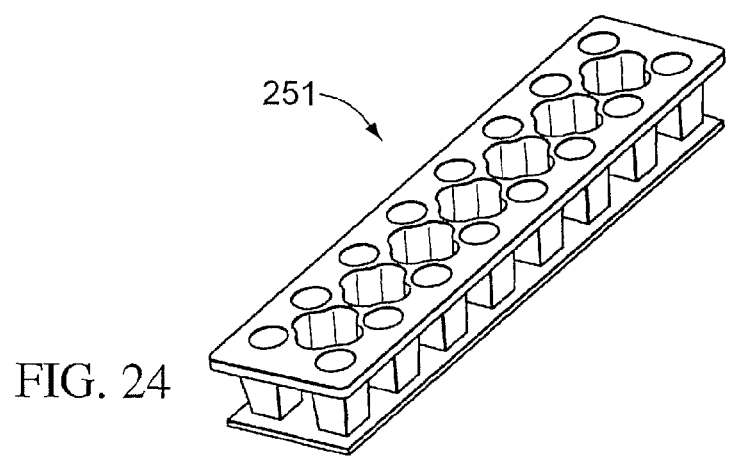
FIG. 24 depicts another sample block segments formed by metal injection molding in accordance with the present teachings.

| Thermal Block Material | FIG. 22 | FIG. 23A & 23B | FIG. 24 |
|---|---|---|---|
| Copper | 5.53 | 9.3 | 8.43 |
| Aluminum | 7.71 | 12.91 | 11.82 |
| Silver | 7.81 | 13.14 | 11.94 |

In various embodiments, the sample blocks and sample block segments described herein can be manufactured by MIM. The sample blocks and sample block segments formed by MIM can include copper, silver, aluminum, and/or gold. The sample blocks and sample block segments formed by MIM can provide substantial temperature uniformity throughout the array of biological samples contained in the array of sample wells coupled to the block for thermal cycling.

In various embodiments, methods for thermally cycling biological sample can be provided by the present teachings by providing the sample blocks and sample block segments produced by a MIM process such that heating and cooling of the sample blocks and sample block segments provides substantial temperature uniformity throughout the plurality of biological samples contained in the plurality of sample wells. The heating can be provided by heat from a resistive heater. In various embodiments, the cooling can be provided by pumping heat out with the thermoelectric module, which can be also be used for providing bias heat during heating cycles. In various embodiments, the cooling can be provided by spinning the block thereby convectively dissipating heat from the sample blocks and sample block segments to the environment during cooling cycles. For example, the sample blocks and/or sample block segments can be disk-like in shape and provide concentric rings of holes to receive the sample wells. The disk can spin along the central axis creating a convective current over the thermal block. Alternatively, the sample blocks and/or sample block segments of any shape can spin along an axis balanced by another sample block and/or sample block segment to provide a convective current similar to a centrifuge. In various embodiments, cooling can be achieved by providing forced gas, such as air or nitrogen, to contact the sample blocks and/or sample block segments. The forced gas can have ambient temperature or can be chilled to below ambient temperature.

In various embodiments, MIM can provide sample blocks and sample block segments that cannot be produced by machining the thermal block from a solid piece of metal because the MIM sample blocks and sample block segments have a thickness that cannot be uniformly machined such that every one of the plurality of sample wells is surrounded by portions of the sample block having similar thickness. For example, MIM can provide rounded exterior surfaces for contacting the sample wells and rounded exterior surfaces with a flat bottom as in FIGS. 23A and 23B. Alternatively, MIM can provide more than one exterior surface for rigidity while removing interior material other than rounded surfaces for contacting the sample wells as in FIG. 24. Also, MIM can provide multiple segments of sample blocks and sample block segments more rapidly and consistently than machining.

The invention is described above with the aid of embodiments with 96 recesses for receiving a microtiter plate with 96 reaction vessels. The invention is not, however, limited to this number of recesses. Thus for example the reaction vessel receiving element may also have 384 recesses to receive a corresponding microtiter plate. With regard to features of the invention not explained in detail above, express reference is made to the claims and the drawing.

In the embodiments described above, a cooling device with a fluid cooling medium is used. Within the scope of the invention it is also possible to use a gaseous cooling medium, in particular air cooling, Instead of a fluid cooling medium.

Figure 26:
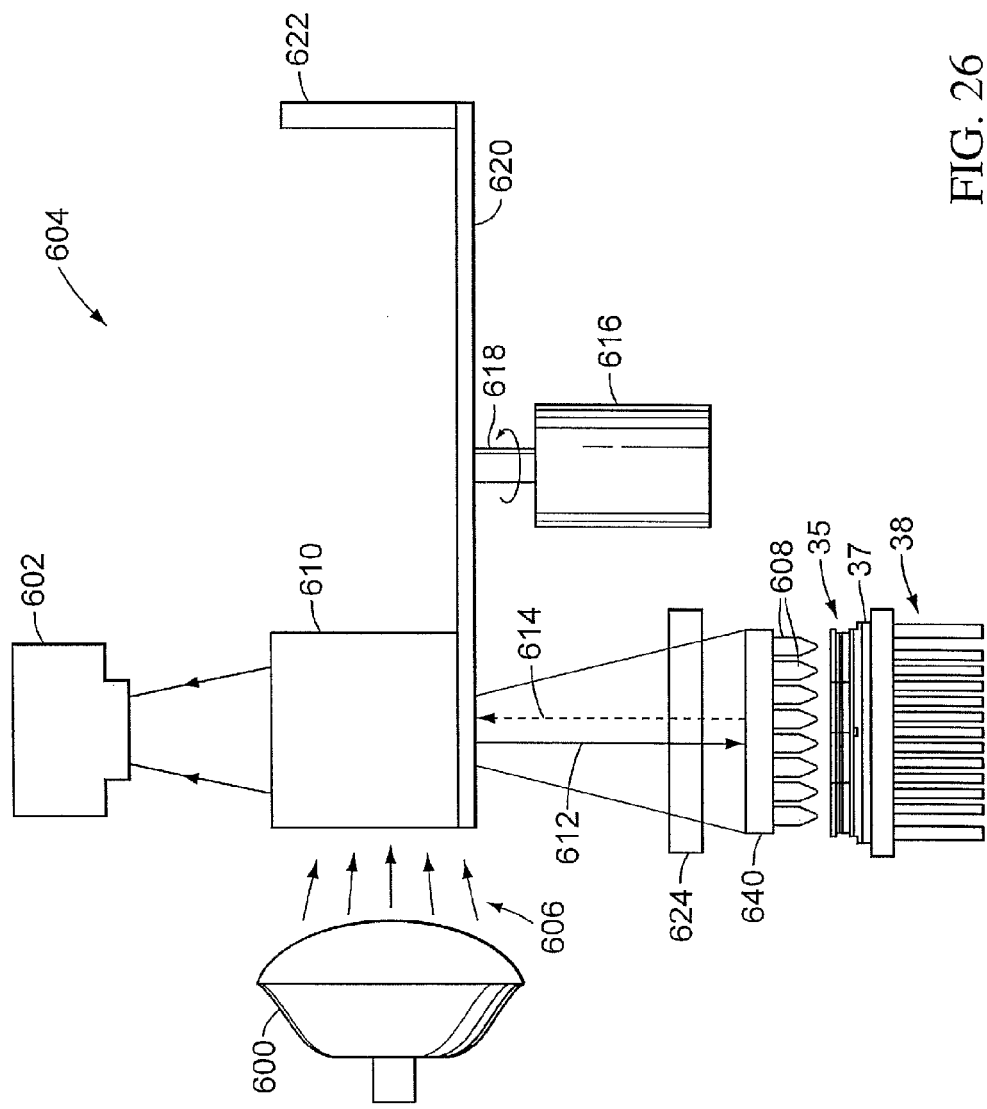
FIG. 26 depicts exemplary imaging optics for fluorescence detection in accordance with the present teachings.
Figure 27A:
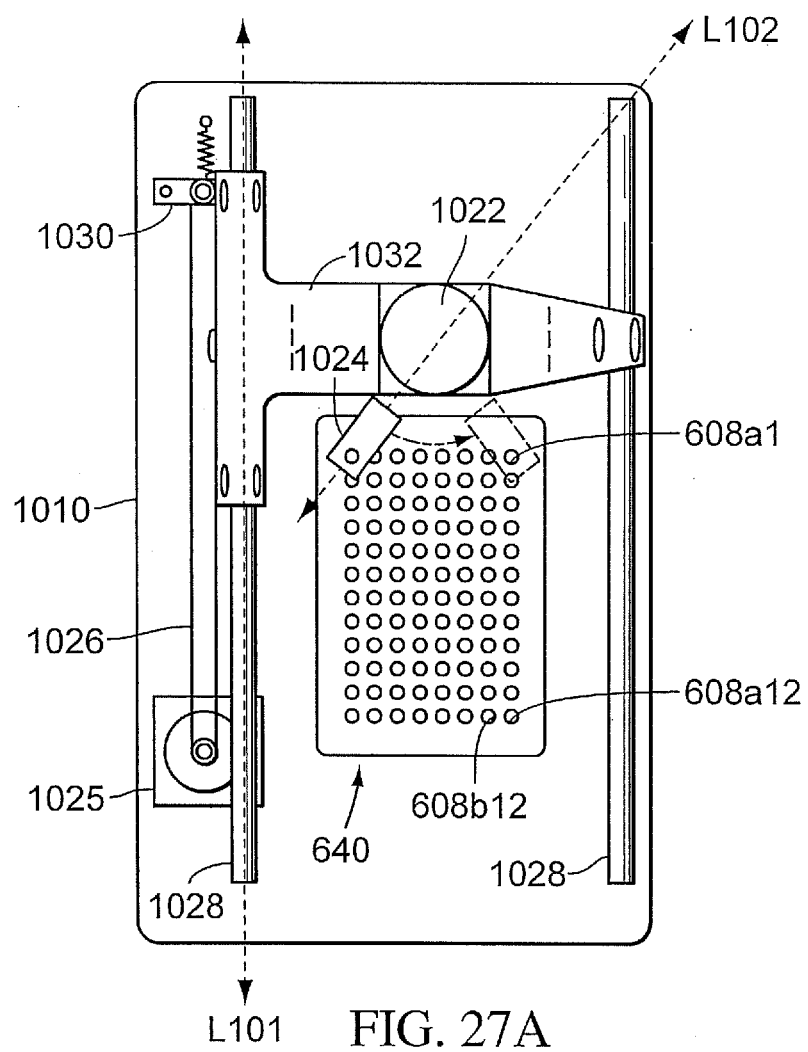
FIGS. 27A-27B depict different embodiments for detection of real-time PCR in the sample block segments.
Figure 27B:
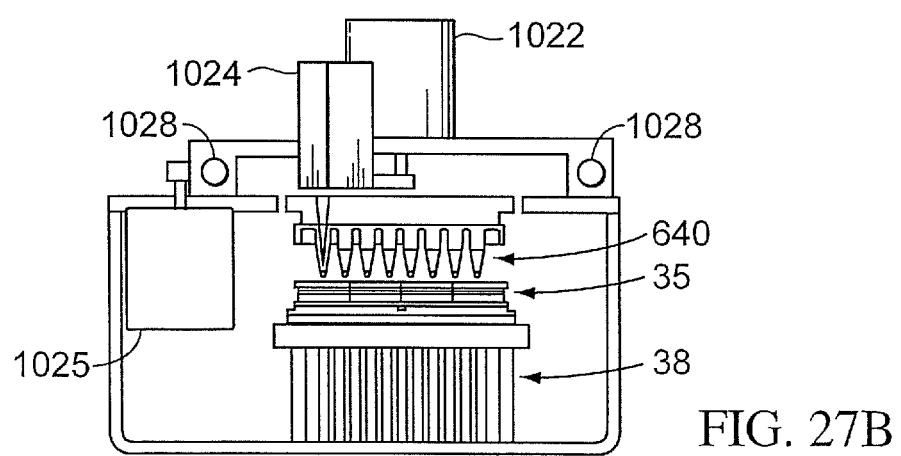

In various embodiments, the sample block with plurality of segments can be combined with an excitation light source and a detector to provide monitoring of real-time PCR in samples in each of the segments. Real-time PCR can be monitored by detecting luminescence (for example, fluorescence, chemiluminescence, etc.) during the thermal cycling. In various embodiments, the monitoring can be provided by imaging optics to optically couple the samples in each of the segments with a detector, such as a CCD. An example of the fluorescence detection with imaging optics embodiment is shown at FIG. 26. In various embodiments, the monitoring can be provided by a scanning head to optically couple the samples in the plurality of segments by movement over the scan head over each of the segments. An example of the fluorescence detection with scanning head embodiment is shown at FIGS. 27A-27B. As shown in FIGS. 27A-27B, the two-dimensional surface of one single microtiter plate positioned over multiple block segments can be effectively scanned by combining a rotation about a single rotational axis with a linear axis scan. FIG. 27A is a top view and FIG. 27B is a cross-sectional side view of a real-time thermal cycler with a scanning head including a rotation arm 1020 with a an axis L102. The rotation arm 1020 is attached to the linear scanner 1010 via a rotational actuator 1022. The linear scanner 1010 is configured to scan a single linear axis L101. As shown, the rotational actuator 1022 rotates about the axis perpendicular to the plane of the paper about the center of the actuator 1022, such that it is generally perpendicular to the plane of the sample. By combining rotational motions of rotational actuator 1022 with linear motions along axis L101 or linear scanner 1010, any location, in particular any sample wells 6081 on the microtiter plate 640 can be optically coupled with the scanning head 1024 by movement over those segments. Scanning head 1024 can contain an optical system with at least one excitation light source and/or at least one detector. Alternatively, the excitation light source and/or detector can be positioned off of the scanning head. For the purpose of illustration, rotational arm 1020 is shown in two different positions. Additionally, according to certain embodiments, there can be multiple rotational arms and rotational actuators, each having at least one associated optical system. As shown in FIGS. 27A and 27B the linear actuator can include a stepper motor 1025 and a belt drive 1026. The stepper motor can be, for example, a NEMA 17 actuator. The belt 1026 can connect the stepper motor 1025 to the spring-based idler take-up arm 1030. When the actuator 1025 is actuated, platform 1032, which is operably connected to belt drive 1026, is translated parallel to axis L101, while traveling on bushings 1028, which can be bronze, plastic or other functionally suitable material. The rotational actuator 1022 is mounted on platform 1032, and is also translated parallel to axis L101. The rotational actuator 1022, which can also be, for example, a NEMA 17 actuator, can rotate about its central axis, causing arm 1020 and scanning head 1024 to sweep out or be aligned to various wells 608 of the microtiter plate 640. As the rotational actuator 1022 is adjusted, the longitudinal axis L102 of arm 1020 can move to different angles relative to linear axis L101, though remaining in common plane for two-dimensional scanning of microtiter plate 640. Thus, for example, combined linear and rotational adjustments can be used to position the scanning head 1024 about well 608a1. This linear axis can then be scanned, such that the wells 608a1-608a12 are scanned. Combined linear and rotational adjustments can then be used to position scanning head 1024 above well 608b12, and then sample row b can be scanned by scanning the linear axis and completing the scanning of the wells 608 over the first segment of block 35. Depending on the different assays and thermal protocols being performed in each segment, the scanning head 1024 can repeat scanning over the first segment or move to the second and/or third segments. Those skilled in the art will appreciate other mechanisms for positioning the scanning head such as arms with elbows, linear-linear actuators, etc. In various alternative embodiments, wherein the segments circular and/or concentric a flying-head scanner can be used. An example of the imaging optics embodiments is shown at FIG. 26. Imaging optics 604 can include a light source 600, optical devices 610, a movable platform 620, a microtiter plate 640, a detector 602, a focusing lens 624, a light blocker 622, and a motor 616. Light source 600 can emit a source beam 606 that is received by one of the optical devices 610. For ease of illustration, FIG. 26 shows one optical device on movable platform 620. However, any number of optical devices can be installed on movable platform 620. A motor 616 can be attached to movable platform 620 with a stem 618. Motor 620 is used to move the movable platform 620 to interpose one of the optical devices 610 into the path of the source beam 606. The motor 616 can also move the movable platform 620 to interpose the light blocker 622 to prevent the source beam 606 from reaching the microtiter plate 640. The optical device 610 receives the source beam 606 and directs a portion as an excitation beam 612 through the focusing lens 624 to the samples in the microtiter plate 640. The samples in the wells 608 of the microtiter plate 640 fit into three segments of the block 35. The excitation beam 612 causes one or more dyes in the samples in each segment to fluoresce and emit light in the form of an emission beam 614. The emission beam 614 can be received by the optical device 610 and then directed by the optical device 610 to a detector 602. The detector 602 generates a data signal that includes information that is representative of the concentration of DNA in the samples in each segment. The segments are associated with different regions on the detector, for example, a CCD. The detector can be calibrated such that the regions corresponding to the assays that are performed in each segment so that detection of the fluorescence is more efficient. According to various embodiments, the light source can be LEDs used to provide improved illumination wavelength uniformity, light power output uniformity, and minimal degradation of output over extended periods of time. Further, LEDs operate at relatively low temperatures and require little or no external cooling. In some embodiments, the size of the light emitted from the light source 600 can be adjusted to be as small as possible to maximize the energy density directed onto the samples. The imaging optics in FIG. 26 illustrate optical devices 610 that can have sets of excitation filters, dichroic mirrors (beamsplitters), and emission filters. Alternatively, filter wheels on the emission side and/or excitation side can provide different excitation and emission light patterns. Similar excitation and emission schemes apply to the scanning head optics.

The term "excitation light source" as used herein refers to a source of irradiance that can provide excitation that results in fluorescent emission. Light sources can include, but are not limited to, LEDs, phosphor coated LEDs, organic LEDs (OLED), phosphorescent OLEDs (PHOLED), inorganic-organic LEDs, LEDs using quantum dot technology, and LED arrays. Alternatively, the light sources can include white light, halogen lamp, lasers, solid state laser, laser diode, micro-wire laser, diode solid state lasers (DSSL), vertical-cavity surface-emitting lasers (VCSEL), thin-film electroluminescent devices (TFELD), filament lamps, arc lamps, gas lamps, and fluorescent tubes. Light sources can have high radiance, such as lasers, or low radiance, such as LEDs. Radiance refers to light emitted and can be measured in units of watts per centimeter squared per steradian. Lasers have high radiance since they emit light in substantially a single direction. LEDs have low radiance since they typically emit light into 2 pi steradians. The different types of LEDs mentioned above can have a medium to high radiance.

The term "detector" as used herein refers to any component, portion thereof or system of components that can detect light including a charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for processing biological or chemical samples comprising:
    denaturing samples in a first portion of a microtiter plate received in a sample block at a temperature $T_{d1}$ by heating a first zone of the sample block, wherein a first thermo electric cooling device (TEC) provides heating and cooling;
    denaturing samples in a second portion of the microtiter plate at a temperature $T_{d2}$ by heating a second zone of the sample block, wherein a second thermo electric cooling device (TEC) provides heating and cooling,
    providing at least one control unit electrically connected to the first thermo electric cooling device (TEC) and the second thermo electric cooling device (TEC), wherein the at least one control unit (a) stores temperatures $T_{d1}$ and $T_{d2}$, and (b) controls the first thermo electric cooling device (TEC) and the second thermo electric cooling device (TEC) to maintain the first portion of the microtiter plate at temperature $T_{d1}$ and maintain the second portion of the microtiter plate at temperature $T_{d2}$; and
    further wherein the first zone and the second zone are thermally decoupled from one another and each of the first TEC and the second TEC are independently actuatable from the other.

2. The method of claim 1, wherein the first thermo electric cooling device provides coarse heating of the first zone to a temperature near $T_{d1}$ and a first heating element provides fine heating of the first zone to about $T_{d1}$.

3. The method of claim 1, wherein the second thermo electric cooling device provides coarse heating of the second zone to a temperature near $T_{d2}$ and a second heating element provides fine heating of the second zone to about $T_{d2}$.

4. The method of claim 1, further comprising denaturing samples in a third portion of the microtiter plate at a third temperature $T_{d3}$ by heating a third zone of the sample block, wherein the third zone is thermally decoupled from the first zone and the second zone, $T_{d2} \neq T_{d3}$ and $T_{d1} > T_{d2}$, wherein a third thermo electric cooling device (TEC) provides heating and cooling, and wherein the at least one control unit (a) stores temperatures $T_{d3}$, and (b) controls the third thermo electric cooling device (TEC) to maintain the third portion of the microtiter plate at temperature $T_{d3}$.

5. The method of claim 1, further comprising denaturing samples in a third portion of the microtiter plate at a third temperature $T_{d3}$ by heating a third zone of the sample block, wherein the third zone is thermally decoupled from the first zone and the second zone, $T_{d1} \neq T_{d2}$ and $T_{d1} < T_{d2}$, wherein a third thermo electric cooling device (TEC) provides heating and cooling, and wherein the at least one control unit (a)

stores temperatures $T_{d3}$, and (b) controls the third thermo electric cooling device (TEC) to maintain the third portion of the microtiter plate at temperature $T_{d3}$.

6. The method of claim 1, further comprising:
annealing samples in the first portion of the microtiter plate at a temperature $T_{a1}$ by cooling the first zone of the sample block; and
annealing samples in the second portion of the microtiter plate at a temperature $T_{a2}$ by cooling the second zone of the sample block, wherein $T_{a2}$ is not equal to $T_{a1}$.

7. The method of claim 6, further comprising:
elongating samples in the first portion of the microtiter plate at a temperature $T_{e1}$ by heating the first zone of the sample block; and
elongating samples in the second portion of the microtiter plate at a temperature $T_{e2}$ by heating the second zone of the sample block, wherein $T_{e2}$ is not equal to $T_{e1}$.

8. The method of claim 1, further comprising:
repeating for a first number of cycles at least one of the steps of denaturing, annealing, and elongating samples in the first portion of the microtiter plate; and
repeating for a second number of cycles at least one of the steps of denaturing, annealing, and elongating samples in the second portion of the microtiter plate, wherein the first number of cycles is not equal to the second number of cycles.

9. The method of claim 6, wherein a rate of cooling the first zone to anneal samples in the first portion of the microtiter plate is not equal to the rate of cooling the second zone to anneal samples in the second portion of the microtiter plate.

10. The method of claim 1, wherein a ramp rate to $T_{d1}$ is not equal to a ramp rate to $T_{d2}$.

11. The method of claim 1, wherein a volume of the samples in the first portion of a microtiter plate is different than a volume of the samples in the second portion of the microtiter plate.

12. The method of claim 6, wherein a residence time for annealing samples in the first portion of the microtiter plate is different than a residence time for annealing samples in the second portion of the microtiter plate.

13. The method of claim 7, wherein a residence time for elongating samples in the first portion of the microtiter plate is different than a residence time for elongating samples in the second portion of the microtiter plate.

14. The method of claim 1, further comprising denaturing samples in a third portion of the microtiter plate, wherein the samples in the first, second, and third portions of the microtiter plate undergo different thermal and chemistry protocols.

15. The method of claim 1, further comprising independently amplifying three or more types of targets simultaneously using different thermal and chemistry protocols for each type of target.

16. The method of claim 15, wherein the microtiter plate comprises six portions and the six portions are used for independent zonal amplification.

17. The method of claim 1, wherein the first zone of the sample block comprises a first set of reaction vessel receiving elements, and wherein the second zone of the sample block comprises a second set of reaction vessel receiving elements.

18. The method of claim 1, wherein the sample block comprises a first sample block segment corresponding to the first zone, and wherein the sample block comprises a second sample block segment corresponding to the second zone, the first sample block segment and the second sample block segment being separate from each other.

19. The method of claim 18, wherein the first sample block segment comprises a first set of reaction vessel receiving elements, and wherein the second sample block segment comprises a second set of reaction vessel receiving elements.

20. The method of claim 1, wherein a temperature difference between $T_{d1}$ and $T_{d2}$ ranges from 5° C. to 15° C.

21. The method of claim 1, wherein a temperature difference between $T_{a1}$ and $T_{a2}$ ranges from 5° C. to 15° C.

22. The method of claim 1, further comprising maintaining the temperature of the first zone at a first temperature while maintaining the temperature of the second zone at a second temperature that is different than the first temperature by from 5° C. to 15° C.

23. The method of claim 1, wherein the first zone and the second zone are separated from one another by a gap.

24. The method of claim 1, wherein the first zone and the second zone are separated from one another by a non heat-conducting material.

* * * * *